(12) United States Patent
Coleman et al.

(10) Patent No.: US 10,258,291 B2
(45) Date of Patent: Apr. 16, 2019

(54) SYSTEMS AND METHODS FOR EVALUATION OF NEUROPATHOLOGIES

(71) Applicants: The Regents of the University of California, Oakland, CA (US); The Salk Institute for Biological Studies, La Jolla, CA (US)

(72) Inventors: Todd Prentice Coleman, La Jolla, CA (US); Marcela Mendoza, La Jolla, CA (US); Justin Tantiongloc, San Diego, CA (US); Ricardo Gil Da Costa, San Diego, CA (US); Thomas D. Albright, La Jolla, CA (US); Gene Stoner, La Jolla, CA (US); Raynard Fung, La Jolla, CA (US)

(73) Assignees: The Regents of the University of California, Oakland, CA (US); The Salk Institute for Biological Studies, La Jolla, CA (US)

(*) Notice: Subject to any disclaimer, the term of this patent is extended or adjusted under 35 U.S.C. 154(b) by 548 days.

(21) Appl. No.: 14/441,826

(22) PCT Filed: Nov. 11, 2013

(86) PCT No.: PCT/US2013/069520
§ 371 (c)(1),
(2) Date: May 8, 2015

(87) PCT Pub. No.: WO2014/075029
PCT Pub. Date: May 15, 2014

(65) Prior Publication Data
US 2015/0305686 A1    Oct. 29, 2015

Related U.S. Application Data

(60) Provisional application No. 61/724,969, filed on Nov. 10, 2012.

(51) Int. Cl.
*A61B 5/0484*    (2006.01)
*A61B 5/0488*    (2006.01)
(Continued)

(52) U.S. Cl.
CPC .......... *A61B 5/7275* (2013.01); *A61B 5/0478* (2013.01); *A61B 5/0484* (2013.01);
(Continued)

(58) Field of Classification Search
CPC ... A61B 5/7275; A61B 5/0478; A61B 5/0484; A61B 5/0488; A61B 5/165; A61B 5/168;
(Continued)

(56) References Cited

U.S. PATENT DOCUMENTS 4,092,981 A    6/1978  Ertl
4,987,903 A    1/1991  Keppel et al.
(Continued)

FOREIGN PATENT DOCUMENTS

CN    101296554 A    10/2008
CN    101500471 A    8/2009
(Continued)

OTHER PUBLICATIONS

Japanese Office Action for Japanese Application No. 2015-541992, dated Sep. 1, 2017, 6 pages.
(Continued)

*Primary Examiner* — Navin Natnithithadha
(74) *Attorney, Agent, or Firm* — Perkins Coie LLP

(57) ABSTRACT

Methods, systems, and devices are disclosed for evaluating vulnerability, disease progression, and treatments in neuropathologies. In one aspect, a method to provide an assessment related to a neurological or neuropsychiatric disorder includes selecting a profile category indicative of one or more aspects of cognitive or sensory functions associated with a neurological or neuropsychiatric disorder, presenting
(Continued)

a sequence of stimuli to a subject, in which the sequence of stimuli is based on the selected profile category, acquiring physiological signals of the subject before, during, and after the presenting of the sequence of stimuli to produce physiological data, and processing the physiological data to generate an information set including one or more quantitative values associated with the selected profile category.

16 Claims, 19 Drawing Sheets

(51) Int. Cl.
    *A61B 5/0478*     (2006.01)
    *A61B 5/0402*     (2006.01)
    *A61B 5/00*     (2006.01)
    *A61B 5/16*     (2006.01)

(52) U.S. Cl.
    CPC ............ *A61B 5/0488* (2013.01); *A61B 5/165* (2013.01); *A61B 5/168* (2013.01); *A61B 5/4082* (2013.01); *A61B 5/4088* (2013.01); *A61B 5/4094* (2013.01); *A61B 5/4848* (2013.01); *A61B 5/7203* (2013.01); *A61B 5/7264* (2013.01); *A61B 5/0402* (2013.01); *A61B 5/4011* (2013.01); *A61B 5/4017* (2013.01); *A61B 2503/40* (2013.01)

(58) Field of Classification Search
    CPC ... A61B 5/4082; A61B 5/4088; A61B 5/4094; A61B 5/4848; A61B 5/7203; A61B 5/7264; A61B 5/0402; A61B 5/4011; A61B 5/4017; A61B 2503/40
    USPC .................................................. 600/544, 545
    See application file for complete search history.

(56) References Cited

U.S. PATENT DOCUMENTS

| | | | |
|---|---|---|---|
| RE34,015 E | 8/1992 | Duffy | |
| 5,406,956 A | 4/1995 | Farwell | |
| 6,032,065 A | 2/2000 | Brown | |
| 6,061,593 A | 5/2000 | Fischell et al. | |
| 6,066,163 A | 5/2000 | John | |
| 6,463,328 B1 | 10/2002 | John | |
| 6,542,081 B2 * | 4/2003 | Torch | A61B 3/0066 340/573.1 |
| 6,832,110 B2 | 12/2004 | Sohmer et al. | |
| 6,947,790 B2 | 9/2005 | Gevins et al. | |
| RE39,539 E * | 4/2007 | Torch | A61B 3/0066 340/573.1 |
| 7,338,455 B2 | 3/2008 | White et al. | |
| D597,676 S | 8/2009 | Copeland et al. | |
| RE41,376 E * | 6/2010 | Torch | A61B 3/0066 340/573.1 |
| RE42,471 E * | 6/2011 | Torch | A61B 3/0066 340/573.1 |
| 7,986,691 B2 | 7/2011 | Park et al. | |
| 7,986,991 B2 | 7/2011 | Prichep | |
| 8,221,330 B2 | 7/2012 | Sarkela et al. | |
| 8,942,813 B1 * | 1/2015 | Hagedorn | A61B 5/0478 607/45 |
| 8,958,882 B1 * | 2/2015 | Hagedorn | A61N 2/006 607/45 |
| 2001/0028309 A1 * | 10/2001 | Torch | A61B 3/0066 340/575 |
| 2003/0013981 A1 | 1/2003 | Gevins et al. | |
| 2003/0032870 A1 | 2/2003 | Farwell | |
| 2003/0073921 A1 | 4/2003 | Sohmer et al. | |
| 2004/0002635 A1 | 1/2004 | Hargrove et al. | |
| 2005/0021104 A1 | 1/2005 | DiLorenzo | |
| 2005/0131288 A1 * | 6/2005 | Turner | A61B 5/0006 600/391 |
| 2005/0143629 A1 | 6/2005 | Farwell | |
| 2005/0273017 A1 | 12/2005 | Gordon | |
| 2006/0183981 A1 | 8/2006 | Skinner | |
| 2007/0100214 A1 | 5/2007 | Steinert | |
| 2007/0106169 A1 | 5/2007 | Fadem | |
| 2007/0191727 A1 | 8/2007 | Fadem | |
| 2008/0221422 A1 | 9/2008 | Rantala | |
| 2008/0249430 A1 | 10/2008 | John et al. | |
| 2009/0214060 A1 | 8/2009 | Chuang et al. | |
| 2009/0216091 A1 | 8/2009 | Arndt | |
| 2009/0220425 A1 | 9/2009 | Moxon et al. | |
| 2009/0227889 A2 | 9/2009 | John et al. | |
| 2010/0010336 A1 | 1/2010 | Pettegrew et al. | |
| 2010/0041962 A1 | 2/2010 | Causevic et al. | |
| 2010/0099954 A1 | 4/2010 | Dickinson et al. | |
| 2010/0274152 A1 | 10/2010 | McPeck et al. | |
| 2011/0109879 A1 | 5/2011 | Palti-Wasserman et al. | |
| 2012/0071781 A1 | 3/2012 | Fadem | |
| 2012/0094315 A1 | 4/2012 | Fryar-Williams | |
| 2012/0150545 A1 | 6/2012 | Simon | |
| 2012/0191000 A1 | 7/2012 | Adachi et al. | |
| 2012/0221075 A1 | 8/2012 | Bentwich | |
| 2012/0253163 A1 | 10/2012 | Afanasewicz et al. | |
| 2015/0045606 A1 * | 2/2015 | Hagedorn | A61B 5/0478 600/13 |
| 2015/0051663 A1 * | 2/2015 | Hagedorn | A61N 2/006 607/45 |
| 2015/0112409 A1 * | 4/2015 | Hagedorn | A61B 5/0006 607/62 |

FOREIGN PATENT DOCUMENTS

| | | |
|---|---|---|
| EP | 1468646 A2 | 10/2004 |
| JP | 2008503261 A | 2/2008 |
| JP | 2009521246 A | 6/2009 |
| JP | 2009542276 A | 12/2009 |
| JP | 2010526379 A | 7/2010 |
| JP | 2011186667 A | 9/2011 |
| KR | 20060085543 A | 7/2006 |
| KR | 20120111030 A | 10/2012 |
| WO | WO-2009044271 A2 | 4/2009 |
| WO | 2011109716 A2 | 9/2011 |
| WO | WO-2011160222 A1 | 12/2011 |

OTHER PUBLICATIONS

Chinese Office Action for Chinese Application No. 201380058415. 8; dated Oct. 18, 2017, 13 pages.
Pilgreen, KL, "Physiologic, medical, and cognitive correlates of electroencephalography." In P. L. Nunez (Ed.), Neocortical dynamics and EEG rhythms, pp. 195-248. New York: Oxford University Press, 1995.
Chinese Office Action for Chinese Application No. 201380058185. 5; dated Mar. 3, 2017.
Chinese Office Action for Chinese Application No. 201380060011. 2; dated Oct. 8, 2016.
International Search Report and Written Opinion issued in PCT/US2013/069520 by the Korean Intellectual Property Office dated Feb. 24, 2014.
"Statistics: Any Anxiety Disorder Among Adults". National Institute of Mental Health. National Institutes of Health. http://www.nimh.nih.gov/statistics/1ANYDIS_ADULT.shtml.
"What is Schizophrenia?". National Institute of Mental Health. Sep. 8, 2009. National Institutes of Health. http://www.nimh.nih.gov/health/publications/schizophrenia/what-is-schizophrenia.shtml.
Breggin, P.R., A.D.H.D. Is a Misdiagnosis. The New York Times. http://www.nytimes.com/roomfordebate/2011/10/12/are-americans-more-prone-to-adhd/adhd-is-a-misdiagnosis.
Coleman et al., "Epidermal electronics capture of brain event-related (ERP) signal in a 'real-world' target detection task", poster presentation at Society for Neuroscience Annual Meeting, Oct. 14, 2012.
Garrido et al. "The mismatch negativity: A review of underlying mechanisms," Clinical Neurophysiology, Mar. 2009, 120, 453-463.

(56) References Cited

OTHER PUBLICATIONS

Gil Da Costa, et al. "Support for a non-human primate model of schizophrenia: acute subanesthetic ketamine reduces mismatch negativity (MMN) and P3", poster presentation at Society for Neuroscience Annual Meeting, Nov. 13, 2011.
Heekeren et al. "Mismatch negativity generation in the human 5HT2A agonist and NMDA antagonist model of psychosis." Psychopharmacology (Berl). Jul. 2008; 199(1): 77-88.
Huang et al. "Stimulus dependency and mechanisms of surround modulation in cortical area MT," Journal of Neuroscience Dec. 17, 2008, 28 (51) 13889-13906.
Javitt, et al. "Demonstration of mismatch negativity in the monkey," Aug. 1992 Electroencephalography and Clinical Neurophysiology. 83, 87-90.
Johnstone, et al. "Predicting schizophrenia: findings from the Edinburgh High-Risk Study," The British Journal of Psychiatry, Jan. 2005, 186 (1) 18-25.
Kim, D.-H. et al., "Epidermal Electronics", *Science*, vol. 333, 2011, pp. 838-843.
Kim, S. et al., "Efficient Bayesian Inference Methods via Convex Optimization and Optimal Transport", Information Theory Proceedings (ISIT), 2013 IEEE International Symposium, pp. 2259-2263.
Liao, L.-D. et al., "Biosensor technologies for augmented brain-computer interfaces in the next decades," Proc. IEEE, vol. 100, 2012, pp. 1553-1566.
Lieberman, J. A. et al., "Effectiveness of antipsychotic drugs in patients with chronic schizophrenia," The New England Journal of Medicine, Sep. 2005, 353, 1209-1223.
Ma, R. et al., "Generalizing the Posterior Matching Scheme to Higher Dimensions via Optimal Transportation", Allerton Conference on Communication, Control, and Computing, Sep. 2011, 7 pages.
Makeig, S. et al., "Evolving signal processing for brain-computer interfaces," Proc. IEEE, vol. 100, 2012, pp. 1567-1584.
Näätänen, R. et al. "'Primitive intelligence' in the auditory cortex," Trends in Neurosciences, Jun. 2001, 24, 283-288.
Näätänen, R. et al., "The mismatch negativity (MMN)—A unique window to disturbed central auditory processing in ageing and different clinical conditions," Clinical Neurophysiology 2012, vol. 123, 424-458.
Oh, e. g., authorized Officer, Korean Intellectual Property Office, International Search Report and Written Opinion, International Patent Application No. PCT/US2013/069520, dated Feb. 24, 2014, 15 pages.
Omar, C. et al., "A Feedback Information-Theoretic Approach to the Design of Brain-Computer Interfaces", International Journal on Human-Computer Interaction, 27(1), Jan. 2011, pp. 5-23.
Rissanen, J., "Hypothesis selection and testing by the MDL principle," The Computer Journal, vol. 42, No. 4, 1999, pp. 260-269.
Sellers, E. W. et al., "A P300-based brain-computer interface: Initial tests by ALS patients", Clinical Neurophysiology 117 (2006) 538-548.
Shayevitz, O. et al., "Optimal Feedback Communication via Posterior Matching", IEEE Transactions on Information Theory, vol. 57, No. 3, Mar. 2011, pp. 1186-1222.
Shin, J. C., Authorized Officer, Korean Intellectual Property Office, International Search Report and Written Opinion, International Patent Application No. PCT/US2013/064892, dated Apr. 11, 2014, 14 pages.
Sutton et al., "Evoked-potentials correlates of stimulus uncertainty," Science, Nov. 26, 1965, vol. 150, No. 3700, pp. 1187-1188.
Toomey, et al., "Why do children with ADHD discontinue their medication?" Clinical Pediatrics, 2012, 51(8) 763-769.
Umbricht, D. et al., "Ketamine-induced deficits in auditory and visual context-dependent processing in healthy volunteers: implications for models of cognitive deficits in schizophrenia," Arch Gen Psychiatry, Dec. 2000; 57(12):1139-47.
Van Der Stelt, et al. "Application of electroencephalography to the study of cognitive and brain functions in schizophrenia," Schizophrenia Bulletin, Jul. 2007; 33(4): 955-970.
Ward, D. et al., "Fast Hands-free Writing by Gaze Direction", Nature, vol. 418, Aug. 22, 2002, p. 838.
Ward, D.J. et al., "Dasher—a Data Entry Interface Using Continuous Gestures and Language Models.", In proceedings UIST 2000, 10 pages.
Wynn, et al., "Mismatch negativity, social cognition, and functioning in schizophrenia patients," Biological Psychiatry 2010; 67, 940-947.
Zander, T.O. et al., "Towards passive brain-computer interfaces: applying brain-computer interface technology to human-machine systems in general", J. Neural Eng. 8, 2011, pp. 1-5.
International Search Report and Written Opinion issued in PCT/US2013/062491 by the Korean Intellectual Property Office dated Jan. 17, 2014.
International Search Report and Written Opinion issued in PCT/US2013/064892 by the Korean Intellectual Property Office dated Apr. 11, 2014.
Extended European Search Report for European Application No. 13845002.8; dated Apr. 28, 2016.
Extended European Search Report for European Application No. 13852926.8; dated Sep. 28, 2016.
Partial Supplementary European Search Report for European Application No. 13852926.8; dated Jun. 6, 2016.
Chinese Office Action for Chinese Application No. 201380058415.8; dated Dec. 8, 2016.
Vecchio, et al. "The Use of Auditory Event-Related Potentials in Alzheimer's Disease Diagnosis," International Journal of Alzheimer's Disease vol. 2011 (2011), Article ID 653173.
Extended European Search Report for European Application No. 13842699.4; dated May 24, 2016.
Chinese Office Action for Chinese Application No. 201380058415.58; dated Jun. 28, 2018, 2 pages.
Office Action for European Application No. 13852926.8; dated Sepember 6, 2018; 5 pages.
Japanese Final Office Action for Japanese Application No. 2015-541992; dated Jun. 25, 2018; 3 pages.

\* cited by examiner

```
Input parameters
Choose data sets using GUI
Check that stimulus markers are compatible across presentation conditions
Create data structures to hold segmented data
FOR each data set, treatment(s), and presentation condition
        Load data set
        Resample to 1000 Hz if needed
        Remove unnecessary channels
        Re-reference to a pool of electrodes
        Band pass filter (0.1 Hz to 50 Hz)
        Notch filter (60 Hz)
        Determine the deviant and standard stimuli
        Find all deviant stimuli and store data epochs (-200 ms to 600 ms after stimulus onset)
        Find all standard stimuli immediately preceding deviant stimuli and store data epochs
        Artifact rejection
END
Average stored data epochs
Calculate P300 for stimulus 1 (i.e., low intensity), stimulus 2 (high intensity), and combined
Calculate MMN for stimulus 1, stimulus 2, and combined
DC de-trend on both P300 and MMN
Baseline correction on both P300 and MMN
Calculate percentage change (change in amplitude) between each physiological treatment
Extract peaks and mean amplitude from single trials and store
Plot MMN for all electrode channels
Plot P300 for all electrode channels
```

FIG. 6

SYSTEMS AND METHODS FOR EVALUATION OF NEUROPATHOLOGIES

CROSS REFERENCE TO RELATED APPLICATIONS

This patent document is a 35 USC § 371 National Stage application of International Application No. PCT/US2013/069520 filed Nov. 11, 2013, which further claims the benefit of priority of U.S. Provisional Patent Application No. 61/724,969 entitled "METHOD AND APPARATUS FOR EVALUATION OF VULNERABILITY AND/OR PROGRESSIVE PATHOLOGY OF NEUROPSYCHIATRIC DISORDERS IN HUMANS AND FOR ASSESSMENT OF POTENTIAL THERAPEUTIC PHARMACOLOGICAL AGENTS FOR NEUROPSYCHIATRIC DISORDERS IN NON-HUMAN PRIMATE BIOLOGICAL MODELS" filed on Nov. 10, 2012. The entire content of the above patent applications are incorporated by reference as part of the disclosure of this patent document.

TECHNICAL FIELD

This patent document relates to systems, devices, and processes for analyzing brain function.

BACKGROUND

Electroencephalography (EEG) is the recording of electrical activity exhibited by the brain using electrodes positioned on a subject's scalp, forming a spectral content of neural signal oscillations that comprise an EEG data set. For example, the electrical activity of the brain that is detected by EEG techniques can include voltage fluctuations, e.g., resulting from ionic current flows within the neurons of the brain. In some contexts, EEG refers to the recording of the brain's spontaneous electrical activity over a short period of time, e.g., less than an hour. EEG can be used in clinical diagnostic applications including epilepsy, coma, encephalopathies, brain death, and other diseases and defects, as well as in studies of sleep and sleep disorders. In some instances, EEG has been used for the diagnosis of tumors, stroke and other focal brain disorders.

One example of an EEG technique includes recording of event-related potentials (ERPs), which refer to EEG recorded brain responses that are correlated with a given event (e.g., simple stimulation and complex processes). For example, an ERP includes an electrical brain response—a brain wave—related to the sensory, motor, and/or cognitive processing. ERPs are associated with brain measures of perception (e.g., visual, auditory, etc.) and cognition (e.g., attention, language, decision making, etc.). For example, ERPs can also be used as objective measures in the evaluation and monitoring of neurological or neuropsychiatric disorders. A typical ERP waveform includes a temporal evolution of positive and negative voltage deflections, termed components. For example, typical components are classified using a letter (N/P: negative/positive) and a number (indicating the latency, in milliseconds from the stimulus event), for which this component arises.

SUMMARY

Disclosed are systems, devices, and methods that acquire and utilize physiological information (e.g., brain signals) to characterize pathology and/or vulnerability of subjects to a neurological or neuropsychiatric disorder and/or assess treatments for such disorders.

In one aspect, a method to provide an assessment related to a neurological or neuropsychiatric disorder includes selecting a profile category indicative of one or more aspects of cognitive or sensory functions associated with a neurological or neuropsychiatric disorder, presenting a sequence of stimuli to a subject, in which the sequence of stimuli is based on the selected profile category, acquiring physiological signals of the subject before, during, and after the presenting of the sequence of stimuli to produce physiological data, and processing the physiological data to generate an information set including one or more quantitative values associated with the selected profile category.

In another aspect, a method to evaluate the efficacy of a treatment for a neurological or neuropsychiatric disorder includes selecting a profile category indicative of one or more aspects of cognitive or sensory functions associated with a neurological or neuropsychiatric disorder, presenting a sequence of stimuli to a subject undergoing a treatment to the neurological or neuropsychiatric disorder, in which the sequence of stimuli is based on the selected profile category, acquiring physiological signals of the subject before, during, and after the presenting of the sequence of stimuli to produce physiological data, and processing the physiological data to generate an information set including one or more quantitative values associated with the selected profile category indicative of the efficacy of the treatment for the subject.

In another aspect, a system for evaluating neurological or neuropsychiatric disorders includes a stimulus delivery device to produce a sequence of stimuli that is presented to a subject, in which the stimuli includes at least one of a visual, auditory, olfactory, tactile, or gustatory stimulating medium, a sensor device interfaced to the subject to detect physiological signals exhibited by the subject before, during, and after a presentation of the sequence of stimuli, in which the sequence of stimuli is based on a cognitive-sensory profile category indicative of one or more aspects of cognitive or sensory functions associated with a neurological or neuropsychiatric disorder, and a data processing system in communication with the sensor device and structured to include one or more memory units and one or more processors configured to process the physiological signals as physiological data to generate an information set including one or more quantitative values associated with the selected profile category, in which the one or more quantitative values includes a quantitative score depicting a level of the pathology of the neurological or neuropsychiatric disorder.

In some implementations, the disclosed technology includes using specialized physiological signal (e.g., electroencephalography and/or electromyography) acquisition techniques and devices with specialized stimuli presentation structures (e.g., of visual, auditory, somatosensory, tactile, gustatory, etc. stimuli) for acquiring electrophysiological recordings that can be associated with brain activity, and including using specialized analysis techniques (e.g., including signal processing, basic and high level statistics, and classification algorithms) to provide an evaluation of an individual and/or group regarding their vulnerability and/or progressive pathology associated with a neurological or neuropsychiatric disorder of interest, and in some implementations, provide an assessment of the efficacy of a treatment such as a therapeutic drug for the neurological or neuropsychiatric disorder using an animal model.

The subject matter described in this patent document can be implemented in specific ways that provide one or more of the following features. For example, the disclosed methods, systems, and devices provide tools that allow for a more accurate, objective, and rapid additional diagnostic and pathological evaluation in humans, as well as enhance pharmacological research into the neural mechanisms underlying neurological or neuropsychiatric disorders, e.g., opening efficient avenues for advanced drug research. For example, the disclosed technology allows users to elicit, measure, and analyze specific brain markers associated with neurological or neuropsychiatric disorder of interest, e.g., schizophrenia, Alzheimer's disease, among others, and as a result, provides purposeful information regarding progressive pathology, vulnerability, and potential therapeutic drug efficacy and efficiency. Moreover, for example, implementation of the disclosed technology does not require a high level of expertise to operate, and as such, is accessible to a wide range of potential users, e.g., efficiently providing reliable, accurate, and informative results for both expert and naïve users.

BRIEF DESCRIPTION OF THE DRAWINGS

FIG. 6 shows an example of pseudo-code for an exemplary programming analysis process of the disclosed technology.

DETAILED DESCRIPTION

Figure 1A:
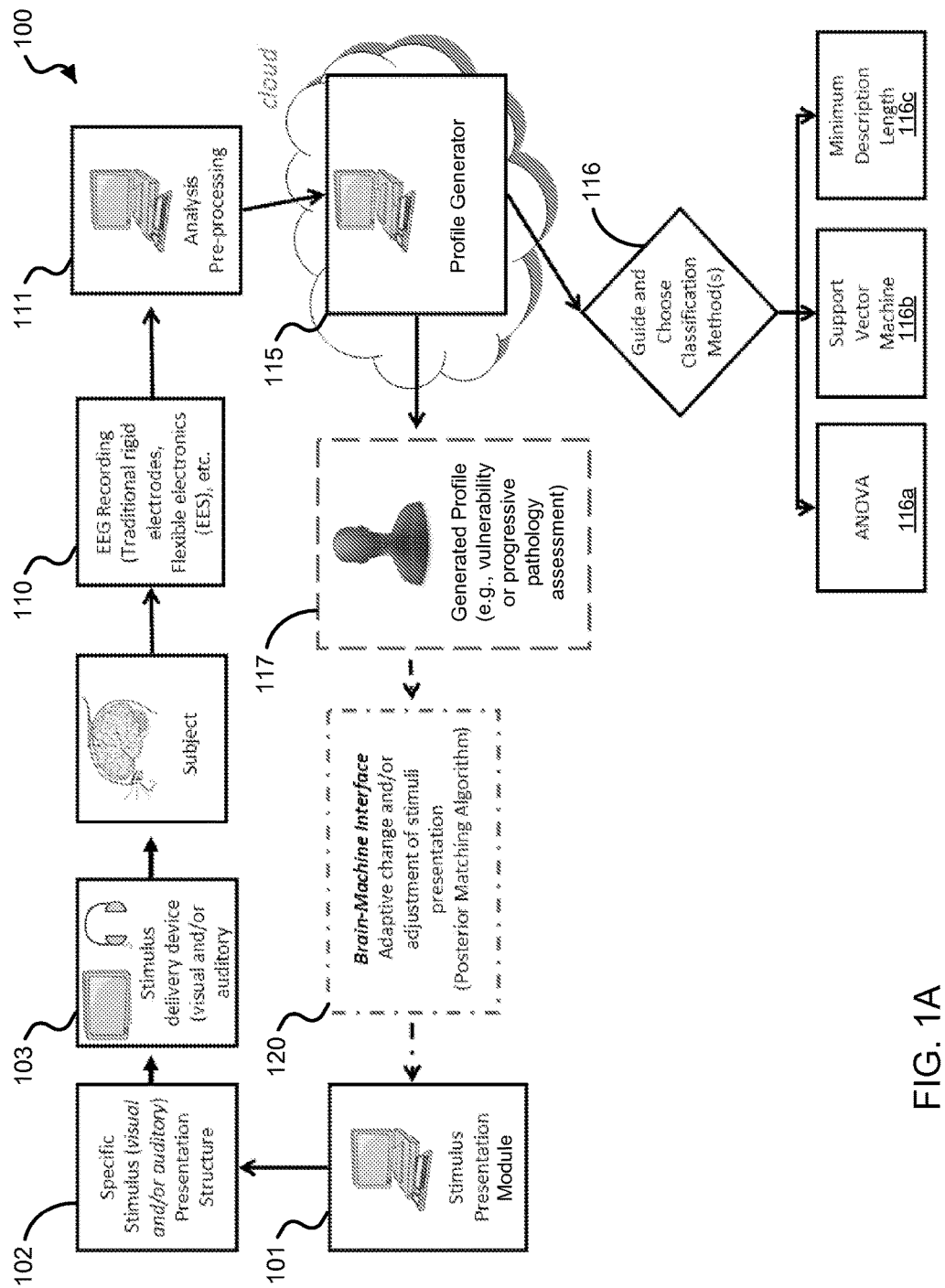
FIG. 1A shows a diagram of an exemplary system of the disclosed technology for acquisition, analysis, and evaluation of physiological signals to produce an individual or group cognitive and/or sensory assessment of a subject, e.g., indicative of the progression of or vulnerability to neuropathologies including specific drug-induced brain effects.

According to the National Institute of Mental Health, neuropsychiatric disorders will continue to affect approximately 46.4 percent of the U.S. adult population, with approximately 22.3 percent of these cases classified as severe. These neuropsychiatric disorders include attention deficit hyperactivity disorder (ADHD), Alzheimer's disease, schizophrenia, depression, dementia, and bipolar disorder, amongst others. While many of these disorders have been characterized in thousands of studies, a lack of consensus and understanding regarding the neural underpinnings of its etiology and the related societal spread still remain. Moreover, although some clinical methods have been introduced to assess vulnerability, diagnose, and treat some neuropsychiatric disorders, there is still a need to develop diagnostic, assessment and treatment techniques providing accuracy, easiness of use, and the ability to guide the users (e.g., physicians/clinicians, researchers, and persons among the general public) to proper courses of action.

For example, in ADHD, many individuals are screened using behavioral assessments that fall within one or more of the following categories, e.g., inattention, hyperactivity, and impulsivity. As such, a vast number of children and adults who meet these criteria often begin medication and behavioral therapy, which can result in years of costly treatment. For example, many of these medications are psycho-stimulants, which for unclear and arguable reasons, can attenuate ADHD-like behavior, despite the fact that they can cause hyperactive/stimulated behavior in normal, healthy individuals. However, use of these drugs may be unable to cure the disorder and bring adverse psychological side effects. For example, the increase of ADHD prevalence (e.g., 9.5 percent of U.S. children) has been attributed to better diagnostic techniques, as well as to high rates of misdiagnoses, e.g., which may be due to the subjectivity of behavioral assessments. Whatever the case, behavioral assessments alone—which are typically subjective—are insufficient as sole measuring tools for ADHD diagnosis and ADHD drug treatment.

Instead of behavioral measures alone, additional and integrative measures, such as physiological measures, can be used for vulnerability assessments, diagnosis, and courses of treatment of neuropsychiatric disorders. For example, by doing so, research and medical communities can have a better understanding of the causes and mechanisms of neuropsychiatric disorders, e.g., including ADHD, and therefore strengthen their ability to develop more efficient lines of research, monitoring, and applied therapies. The disclosed technology can provide techniques for assessing neuropsychiatric vulnerabilities and pathologies in subjects using objective measures and creating new analytical methodologies for pharmacological research and development to mediate and/or cure these disorders.

Disclosed are systems, devices, and methods that acquire and utilize physiological information (e.g., brain signals) to characterize pathology and/or vulnerability of subjects to a neurological or neuropsychiatric disorder and/or assess treatments for such disorders.

In some implementations, the disclosed technology includes using specialized physiological signal (e.g., electroencephalography and/or electromyography) acquisition techniques and devices with specialized stimuli presentation structures (e.g., of visual, auditory, olfactory, somatosensory, tactile, gustatory, etc. stimuli) for acquiring electrophysiological recordings that can be associated with brain activity, and including using specialized analysis techniques (e.g., including signal processing, basic and high level statistics, and classification algorithms) to provide an evaluation of an individual and/or group regarding their vulnerability and/or progressive pathology associated with a neuropsychiatric disorder of interest, and in some implementations, an assessment of the efficacy of potential therapeutic drugs for neuropsychiatric disorders using a non-human primate animal model.

For example, in some implementations, the disclosed technology can provide an automated, all-inclusive system for stimulus presentation, data acquisition, local and/or remote data processing and analysis, and user results output. Such systems can be used to reduce or eliminate the complications associated with electrophysiological recording and analysis techniques, thereby providing users (e.g., including, but not limited to clinicians, pharmaceutical researchers and general consumers) with a non-invasive and rapid diagnostic testing tool for assessment of pathology and/or vulnerability of neurological or neuropsychiatric disorders in humans (or other animals) and efficacy of treatments for such disorders (e.g., including potential therapeutic drugs).

In one aspect, the disclosed technology includes a method to provide an assessment related to a neurological or neuropsychiatric disorder. The method includes selecting a profile category indicative of one or more aspects of cognitive or sensory functions associated with a neurological or neuropsychiatric disorder. The method includes presenting a sequence of stimuli to a subject, in which the sequence of stimuli is based on the selected profile category. The method includes acquiring physiological signals of the subject before, during, and after the presenting of the sequence of stimuli to produce physiological data. The method includes processing the physiological data to generate an information set including one or more quantitative values associated with the selected profile category. For example, the quantitative values of the generated information set include a quantitative score depicting a level of vulnerability to or progressive pathology of the neurological or neuropsychiatric disorder. For example, the selected profile category can be indicative of one or more of a variety of neurological or neuropsychiatric disorders that affect one or more aspects of cognitive or sensory functions, e.g., including, but not limited to, attention, memory, learning ability, confabulation characteristics, pattern integration ability, semantic integration ability, target detection ability, emotional valence, preference, or awareness state. Neuropsychiatric disorders and neurological disorders and/or neurodegenerative diseases can be evaluated and characterized using the disclosed technology. Examples of such neuropsychiatric disorders and neurological disorders and/or neurodegenerative diseases include, for example, but are not limited to, attention deficit hyperactivity disorder (ADHD), autism spectrum disorder (ASD), Alzheimer's disease, dementia, depression, bipolar disorder, schizophrenia, epilepsy, multiple sclerosis (MS), Parkinson's disease, and Huntington's disease. Additionally, for example, the method can be implemented to provide a quantitative assessment indicative of one or more aspects of cognitive or sensory functions associated with a neurological disorders and dysfunctions, including, but not limited to, stroke, aphasia, Down's syndrome, Velo-cardio-facial (DiGeorge) syndrome, coma, chronic or acute drug or alcohol use, as well as other neurological disorders and dysfunctions exhibiting changes brain signal markers (e.g., ERPs).

In some implementations of the method to provide an assessment related to a neurological or neuropsychiatric disorder, for example, the processing of the physiological data to generate the information set can include identifying a time interval associated with the physiological signals based on the presented stimuli and the selected profile category, grouping the physiological data corresponding to the time interval into one or more grouped data sets, and providing a statistical measure of a relationship across or within the grouped data sets to generate the one or more quantitative values for the selected profile category. In some examples, the grouping can be determined based on at least one of a pre-assigned category of the individual stimulus or an associative relationship of consecutive stimuli. In other implementations of the method to provide an assessment related to a neurological or neuropsychiatric disorder, for example, the processing of the physiological data to generate the information set can include identifying a time interval associated with the physiological signals based on the presented stimuli and the selected profile category, grouping the physiological data corresponding to the time interval into one or more grouped data sets, and providing a statistical measure of a relationship across or within the grouped data sets using previous physiological data acquired from the subject or other subjects to generate the one or more quantitative values for the selected profile category. And in other implementations of the method to provide an assessment related to a neurological or neuropsychiatric disorder, for example, the processing of the physiological data to generate the information set can include identifying a time interval associated with the physiological signals based on the presented stimuli and the selected profile category, grouping the physiological data corresponding to the time interval into one or more initial grouped data sets, classifying each stimulus of the sequence of stimuli presented to the subject using a statistical test involving the initial grouped data sets, based on the classified stimuli, re-grouping the physiological data corresponding to the time interval into one or more grouped data sets, and providing a statistical measure of a relationship across or within the grouped data sets to generate the one or more quantitative values for the selected profile category.

In some implementations of the method to provide an assessment related to a neurological or neuropsychiatric disorder, for example, the method can further include forming a modified sequence of stimuli using the generated information set for the subject, and presenting the modified sequence of stimuli to the subject. Additionally, for example, the method can further include acquiring physiological signals of the subject before, during, and after the presenting the modified sequence of stimuli to produce new physiological data, and processing the new physiological data to generate an augmented information set including one or more augmented quantitative values associated with the selected profile category. In some implementations of the method, the acquiring does not involve a behavioral response by the subject and the processing does not include processing behavioral data to generate the information set. While in other implementations, for example, the method can further include acquiring behavioral signals of the subject before, during, and after the presenting the sequence of stimuli to produce behavioral data, and processing the behavioral data with the physiological data to generate the information set including the one or more quantitative values associated with the selected profile category.

In another aspect, the disclosed technology includes a method to evaluate the efficacy of a treatment for a neurological or neuropsychiatric disorder. The method includes selecting a profile category indicative of one or more aspects of cognitive or sensory functions associated with a neurological or neuropsychiatric disorder. The method includes presenting a sequence of stimuli to a subject undergoing a treatment to the neurological or neuropsychiatric disorder, in which the sequence of stimuli is based on the selected profile category. The method includes acquiring physiological signals of the subject before, during, and after the presenting of the sequence of stimuli to produce physiological data. The method includes processing the physiological data to generate an information set including one or more quantitative values associated with the selected profile category indicative of the efficacy of the treatment for the subject. For example, the quantitative values of the generated information set include a quantitative score depicting a level of pathology of the neurological or neuropsychiatric disorder of the subject undergoing the treatment. For example, the treatment used to treat the subject, e.g., including before and during the implementation of the method to evaluate its efficacy, can include a pharmacological agent, an electroconvulsive therapy, a cognitive rehabilitation therapy, or a surgical treatment.

For example, a pharmacological agent (e.g., complex drugs or compounds) can be used to treat, recover, reduce or ameliorate pathological symptoms in wide range of neurological or neuropsychiatric disorders Implementations of the method can be used in pharmacological research, e.g., assessing the effects of both symptom's inducing and symptom's recovery drugs, by evaluating modulations of correlated physiological and/or behavioral signals that are acquired from the subject. For example, an electroconvulsive therapy (ECT) is an intervention treatment that includes the application of electrical current to induce seizures in subjects undergoing ECT treatment (e.g., in neuropsychiatric patients) as a way to provide relief (e.g., in some instances in depression and schizophrenia). For example, cognitive rehabilitation therapy (CRT) is the use of behavioral training protocols as a means to improve recovery from sensory and/or cognitive deficits. CRT includes behavioral stimulation, leading to neural training and priming that has been shown to improve recovery from deficits in a wide variety of mental disorders (e.g., such as schizophrenia, ADHD, Aphasia, depression, etc.). Examples of CRT treatments can include cognitive remediation therapy or cognitive enhancement therapy, were the behavioral training can be guided (and or assessed) by a computer (machine system). For example, CRT treatments can implemented in conjunction with the disclosed technology by correlating the CRT protocol with the subject's own physiological and behavioral measures to automate and optimize the procedure and outcome. Additionally, for example, CRT treatments can also be complemented with pharmacological agents based treatments. For example, the efficacy of surgical treatments evaluated using the method, e.g., in which a physiological measure (e.g., EEG) of brain responses would be acquired while performing a surgical intervention, which can be used to provide way to monitor both the patient's state and to probe responses from stimulation and intervention effects of specific brain areas, as a way to better guide surgery.

In implementations of the method, for example, the subjects can include human subjects and non-human subjects. For example, the non-human subject can include primates, porcine subjects, and murine subjects, among others. In some implementations, for example, the method can further include injecting or infusing a pharmacological agent at a particular dose to the subject. In some implementations of the method to evaluate the efficacy of the treatment for a neurological or neuropsychiatric disorder, for example, the processing of the physiological data to generate the information set can include identifying a time interval associated with the physiological signals based on the presented stimuli and the selected profile category, grouping the physiological data corresponding to the time interval into one or more grouped data sets, and providing a statistical measure of a relationship across or within the grouped data sets to generate the one or more quantitative values for the selected profile category. In some examples, the grouping can be determined based on at least one of a pre-assigned category of the individual stimulus or an associative relationship of consecutive stimuli. In other implementations of the method to evaluate the efficacy of the treatment for a neurological or neuropsychiatric disorder, for example, the processing of the physiological data to generate the information set can include identifying a time interval associated with the physiological signals based on the presented stimuli and the selected profile category, grouping the physiological data corresponding to the time interval into one or more grouped data sets, and providing a statistical measure of a relationship across or within the grouped data sets using previous physiological data acquired from the subject or other subjects to generate the one or more quantitative values for the selected profile category.

In some implementations of the method to evaluate the efficacy of the treatment for a neurological or neuropsychiatric disorder, for example, the method can further include forming a modified sequence of stimuli using the generated information set for the subject, and presenting the modified sequence of stimuli to the subject. Additionally, for example, the method can further include acquiring physiological signals of the subject before, during, and after the presenting the modified sequence of stimuli to produce new physiological data, and processing the new physiological data to generate an augmented information set including one or more augmented quantitative values associated with the selected profile category. In some implementations of the method, the acquiring does not involve a behavioral response by the subject and the processing does not include processing behavioral data to generate the information set.

While in other implementations, for example, the method can further include acquiring behavioral signals of the subject before, during, and after the presenting the sequence of stimuli to produce behavioral data, and processing the behavioral data with the physiological data to generate the information set including the one or more quantitative values associated with the selected profile category.

In another aspect, disclosed technology includes a system for evaluating neurological or neuropsychiatric disorders. The system includes a stimulus delivery device to produce a sequence of stimuli that is presented to a subject, in which the stimuli includes at least one of a visual, auditory, olfactory, tactile, or gustatory stimulating medium. The system includes a sensor device interfaced to the subject to detect physiological signals exhibited by the subject before, during, and after a presentation of the sequence of stimuli, in which the sequence of stimuli is based on a cognitive-sensory profile category indicative of one or more aspects of cognitive or sensory functions associated with a neurological or neuropsychiatric disorder. The system includes a data processing system in communication with the sensor device and structured to include one or more memory units and one or more processors configured to process the physiological signals as physiological data to generate an information set including one or more quantitative values associated with the selected profile category, in which the one or more quantitative values includes a quantitative score depicting a level of the subject's vulnerability to or progressive pathology of the neurological or neuropsychiatric disorder.

In some implementations of the system, for example, the data processing system can include a local computer located proximate and in communication with the sensor device to receive the detected physiological signals from the sensor device, in which the local computer is configured to conduct initial processing of the detected physiological signals to produce initial physiological signal data, and a remote computer in communication with the local computer via a communication network or link to receive the initial physiological signal data from the local computer and to process the initial physiological signal data to generate the information set including one or more quantitative values associated with the cognitive-sensory profile category. For example, the local computer can be in communication with the stimulus delivery device and configured to determine the sequence of stimuli to be presented to the subject based on the selected profile category. For example, the local computer can be configured to receive data associated with or derived from the generated information set and to modify the sequence of stimuli to the subject to produce a modified sequence of stimuli that is individualized with respect to the subject. For example, the stimulus delivery device can include a display screen to generate a sequence of images and/or a speaker to generate a sequence of sounds. For example, the stimulus delivery device can include an actuator to generate a sequence of at least one of olfactory, tactile, or gustatory stimuli.

In some implementations of the system, for example, the subject can be undergoing a treatment (e.g., such as pharmacological agent treatment, ECT treatment, a CRT treatment, or a surgical treatment) to the neurological or neuropsychiatric disorder during the detection of the subject's physiological signals. For example, the data processing system can be configured to process the physiological data to generate the information set to include one or more quantitative values associated with the selected profile category indicative of the efficacy of the treatment for the subject. For example, the data processing system is configured to produce a machine procedure based on the generated information set, in which the machine procedure can actuate another device or system to administer the treatment derived from information contained within the generated information set. In some examples, the machine procedure can be used to inject a particular dose of a pharmacological agent or the ECT electrical stimulation in real-time during the implementation of the assessment.

Exemplary Embodiments of the Disclosed Systems, Devices, and Methods

FIG. 1A shows a diagram of an exemplary modular system 100 of the disclosed technology for acquisition, analysis, and evaluation of physiological signals to produce an individual or group cognitive and/or sensory assessment of a subject, e.g., indicative of the progression of or vulnerability to neuropathologies including specific drug-induced brain effects. For example, the system 100 can be implemented to provide a cognitive and/or sensory profile associated with a neurological or neuropsychiatric disorder using only physiological data acquired from the subject, e.g., with no overt behavioral response elicited from the subject. Whereas, in other implementations, the system 100 can be implemented to provide the cognitive and/or sensory profile associated with a neurological or neuropsychiatric disorder using behavioral data or both physiological and behavioral data from the subject. In some implementations, the system 100 can be implemented to provide the cognitive and/or sensory profile associated with a neurological or neuropsychiatric disorder using previously acquired physiological and/or behavioral data from the subject, or other subjects (e.g., group data).

As shown in FIG. 1A, the system 100 is configured to include independent modular units or devices that can be configured in a variety of different embodiments. The system 100 includes a stimulus presentation module 101 to configure a specific stimulus presentation structure 102 to effectuate a presentation of a stimulus or a sequence of stimuli to a subject. In some examples, the stimulus presentation module 101 is embodied in a computing device, e.g., including a processor and memory unit. For example, the stimuli can include any stimulus type, including a visual, auditory, olfactory, tactile, or gustatory stimulating medium. The specific stimulus presentation structure 102 can be configured to include, but is not limited to, a particular type or types of stimuli, the duration of presentation of the stimuli, an inter-stimuli interval, a number of repetitions (if any) of each presentation, magnitude and/or frequency parameters associated with type of stimuli (e.g., intensity of sound or brightness or contrast level of light), a digital marker associated with the presentation of each stimuli, and a label or category of the stimuli (e.g., target or non-target).

The system 100 can include a stimulus delivery module 103 in communication with the stimulus presentation module 101 to present the stimulus or the sequence of stimuli to the subject, e.g., based on the stimulus presentation structure 102. For example, the stimulus delivery module 103 can include at least one of a visual display, an auditory speaker, and an actuator to provide an olfactory, tactile, and/or gustatory stimulus. In some implementations, for example, the stimulus presentation module 101 and the stimulus delivery module 103 can be configured in the same device, e.g., such as a computer or mobile communication and/or computing device.

The system 100 includes a physiological and/or behavioral data acquisition module 110 to acquire physiological signals and/or behavioral signals of the subject before, during, and/or after the presentation of the stimuli or sequence of stimuli via the stimulus delivery module 103. For example, the physiological and/or behavioral data acquisition module 110 can include, but is not limited to, an electroencephalography (EEG) system, an electrocardiography (ECG) system, an electromyography (EMG) system, an electrochemical sensing system, and an eye tracking system, among others. In some implementations, for example, the physiological and/or behavioral data acquisition module 110 can include physiological sensors, e.g., EEG, ECG, EMG, electrochemical, or other types of sensor devices, coupled to a signal acquisition device, e.g., such as an analog or digital amplifier coupled to a memory. For example, the physiological and/or behavioral data acquisition module 110 can be configured in a standard EEG system with rigid electrodes or a portable EEG system using flexible electronics that can be worn on the subject. For example, the physiological and/or behavioral data acquisition module 110 can be configured in a standard EMG system with rigid electrode or a portable EMG system using flexible electronics that can be worn on the subject, e.g., capable of detecting movements associated with drowsiness or facial expressions.

The system 100 includes an analysis pre-processing module 111 to receive the acquired physiological signals and/or behavioral signals as data, and in some implementations, to perform pre-processing analysis techniques on the acquired data. For example, the analysis pre-processing module 111 can be implemented to identify exemplary onset markers in the physiological data (e.g., EEG data), segment the physiological data, filter raw signal data to increase signal to noise, etc. In some implementations, for example, the analysis pre-processing 111 can be embodied in a computer device in communication with an exemplary device or system embodying the physiological and/or behavioral data acquisition module 110. In some implementations, for example, the analysis pre-processing 111 can be configured in the same exemplary device or system that embodies the physiological and/or behavioral data acquisition module 110.

The system 100 includes a profile generation module 115 to process the physiological and/or behavioral data to provide a cognitive or sensory assessment of the subject, or in some examples, of a group. For example, the profile generation module 115 processes the physiological and/or behavioral data to generate an information set 117 that includes one or more quantitative values that are associated with the selected profile category, e.g., such as a score depicting the level of the subject's vulnerability to or progressive pathology of the neurological or neuropsychiatric disorder, or depicting the efficacy of a treatment for the disorder (e.g., which can be specific to the subject and his/her condition).

Figure 1B:
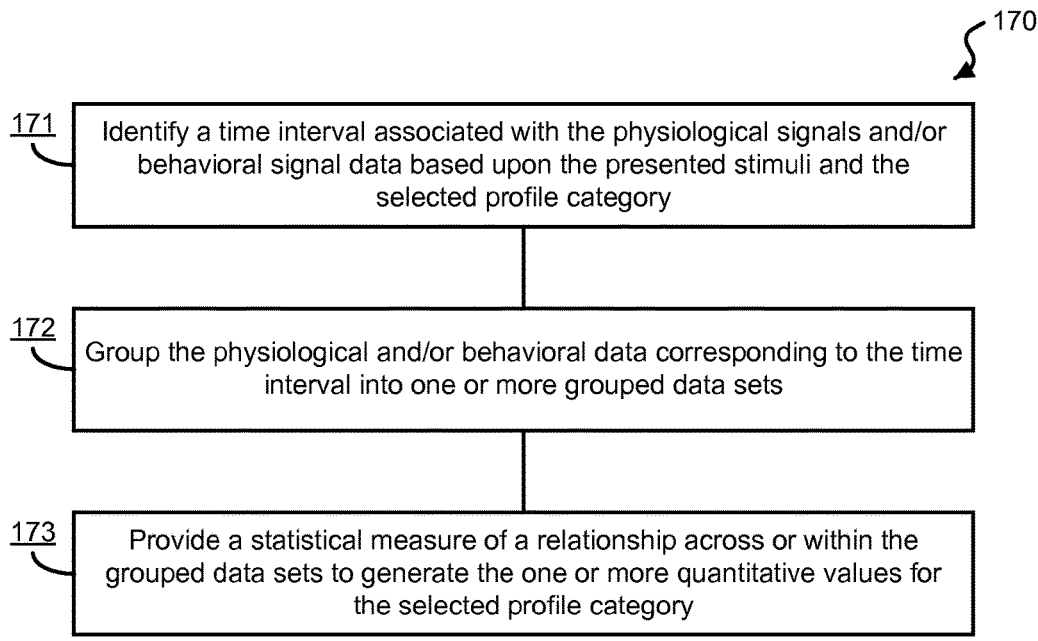
FIGS. 1B-1D show process diagrams of exemplary methods to generate a quantitative information set of an exemplary cognitive and/or sensory profile.

FIG. 1B shows a process diagram of an exemplary method 170 to generate the information set associated with the selected profile category related to the neurological or neuropsychiatric disorder, e.g., implemented by the profile generation module 115. The method 170 can include a process 171 to identify a time interval associated with the physiological signals and/or behavioral signal data based upon the presented stimuli and the selected profile category. For example, a time interval can include contiguous, discontinuous, continuous, discrete, or single time points. The method 170 can include a process 172 to group the data (e.g., physiological and/or behavioral) corresponding to the time interval into one or more grouped data sets. For example, the process 172 can include grouping the physiological and/or behavioral data based on a pre-assigned category of the individual stimulus and/or an associative relationship of consecutive stimuli. The method 170 can include a process 173 to provide a statistical measure of a relationship across or within the grouped data sets to generate the one or more quantitative values for the selected profile category. In some implementations, for example, the method 170 can include a process to enhance the signal of the physiological and/or behavioral data in the grouped data sets.

Figure 1C:
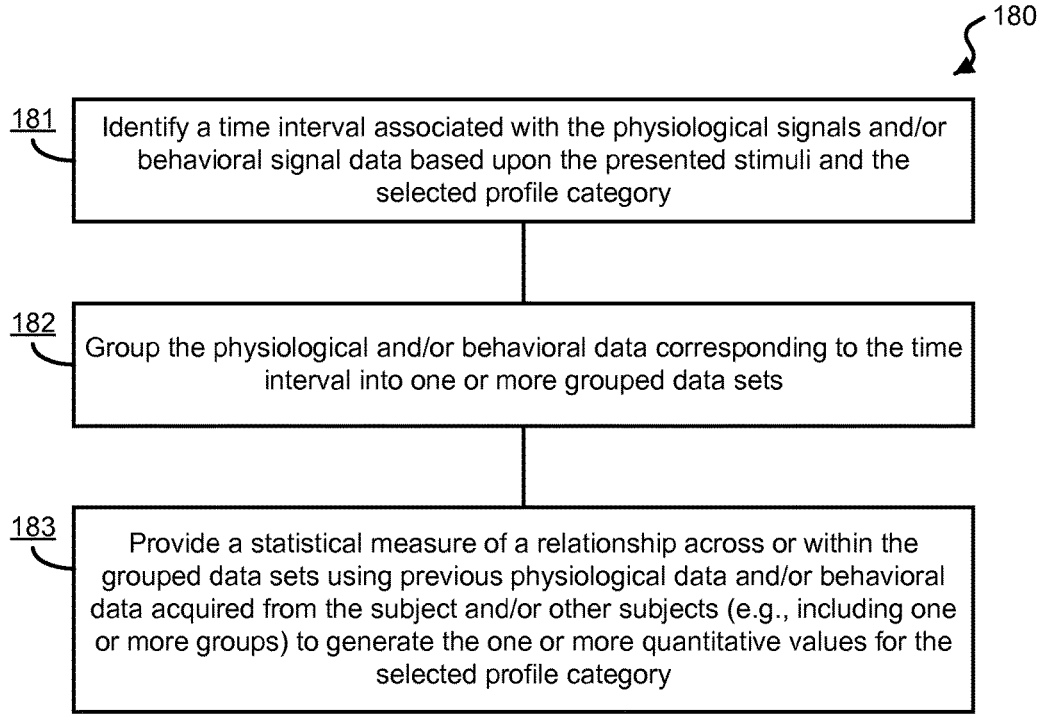

FIG. 1C shows a process diagram of an exemplary method 180 to generate the information set associated with the selected profile category related to the neurological or neuropsychiatric disorder using previous individual and/or group information, e.g., implemented by the profile generation module 115. The method 180 can include a process 181 to identify a time interval associated with the physiological signals and/or behavioral signal data based upon the presented stimuli and the selected profile category. The method 180 can include a process 182 to group the data (e.g., physiological and/or behavioral) corresponding to the time interval into one or more grouped data sets. For example, the process 182 can include grouping the physiological and/or behavioral data based on a pre-assigned category of the individual stimulus and/or an associative relationship of consecutive stimuli. The method 180 can include a process 182 to provide a statistical measure of a relationship across or within the grouped data sets using previous physiological data and/or behavioral data acquired from the subject and/or other subjects (e.g., including one or more groups) to generate the one or more quantitative values for the selected profile category.

Figure 1D:
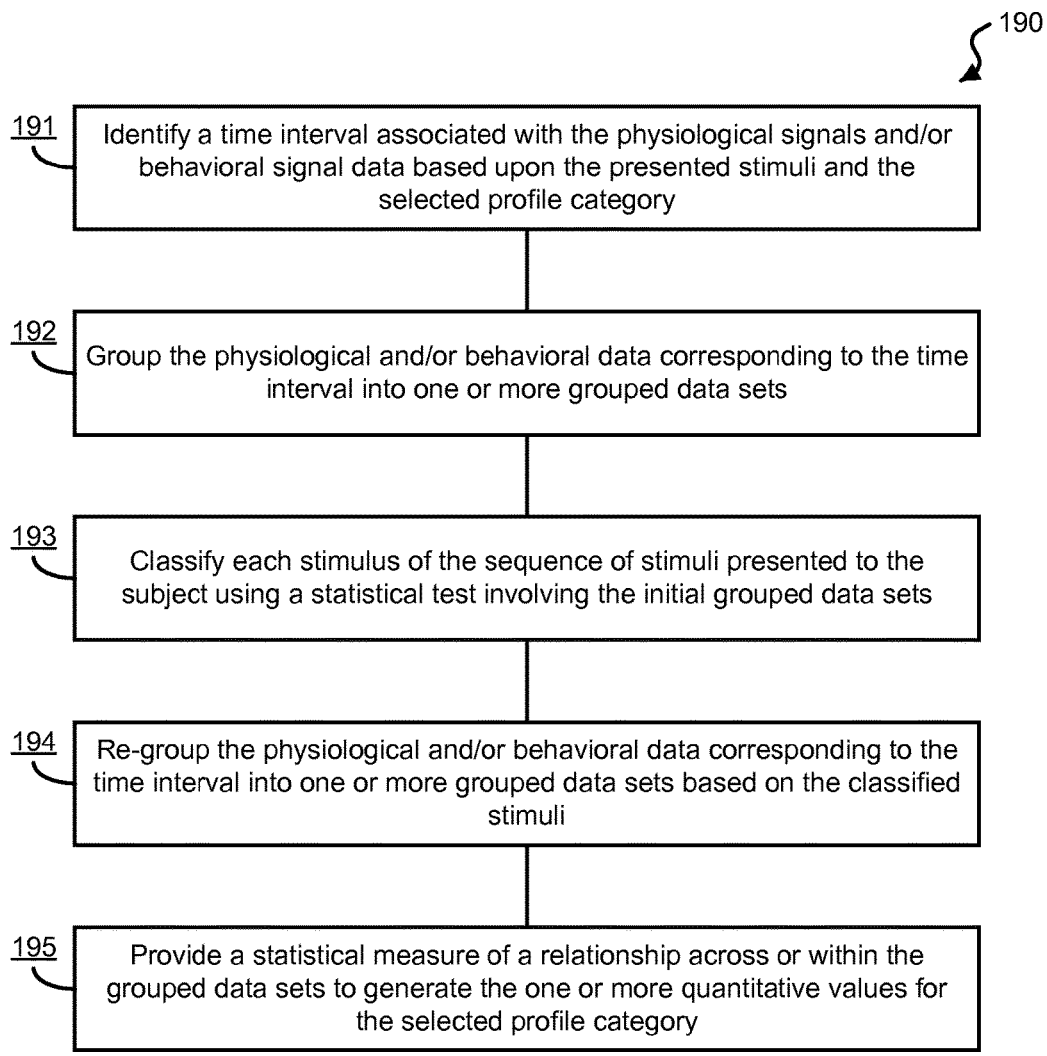

FIG. 1D shows a process diagram of an exemplary method 190 to generate the information set associated with the selected profile category related to the neurological or neuropsychiatric disorder using a guided classification technique, e.g., implemented by the profile generation module 115. The method 190 can include a process 191 to identify a time interval associated with the physiological signals and/or behavioral signal data based upon the presented stimuli and the selected profile category. The method 190 can include a process 192 to group the data (e.g., physiological and/or behavioral) corresponding to the time interval into one or more initial grouped data sets. The method 190 can include a process 193 to classify each stimulus of the sequence of stimuli presented to the subject using a statistical test involving the initial grouped data sets. The method 190 can include a process 194 to re-group the physiological and/or behavioral data corresponding to the time interval into one or more grouped data sets based on the classified stimuli. The method 190 can include a process 195 to provide a statistical measure of a relationship across or within the grouped data sets to generate the one or more quantitative values for the selected profile category.

In some examples, the profile generation module 115 can implement guided classification algorithms with context specific parameters to guide and choose from a variety of classification and statistical methods, e.g., including, but not limited to, ANOVA based techniques 116a, support vector machine based techniques 116b, and minimum description length techniques 116c, among others. In some implementations, the profile generation module 115 can be embodied on a computer system or communication network (referred to as 'the cloud') that includes one or more remote computational processing devices (e.g., servers in the cloud).

The system 100 includes a brain-machine interface module 120 to refine the generated cognitive and/or sensory profiles related to the neurological or neuropsychiatric disorder and/or actuate an interaction between a user and a machine. In one example, the brain-machine interface module 120 can provide a feedback delivery of a new stimulus or multiple stimuli to the stimulus presentation module 101 based on a generated profile 117 (of the individual subject being tested, or previously tested, or a group of subjects that has assessed via the profile generation module 115), e.g., including during an on-going implementation of the system 100. For example, the brain-machine interface module 120 can adaptively change or design stimuli paradigms that optimally extract information from the subject that is analytically processed to maximize a desired objective. For example, the brain-machine interface module can produce a machine procedure based on the generated information set that can be used to actuate another device or system, e.g., such as a device or system to administer the treatment derived from information contained within the generated information set. For example, some implementations of the brain-machine interface module 120 can include, but are not limited to, assisted-learning and target detection applications.

In some implementations of the system 100, the profile generation module 115, the stimulus presentation module 101, the stimulus delivery module 103, and the brain-machine interface module 120 (and in some instances, the data acquisition module 110) can be embodied in a single computing system, e.g., a desktop computer, a laptop computer, or a mobile communications device including a smartphone or tablet. In other implementations, the modules 115, 101, 103, and 120 can be configured in two or more computing devices in communication with each other and including various combinations of the modules 115, 101, 103, and 120.

In some implementations, the system 100 can be configured to just include the physiological and/or behavioral data acquisition module 110 and the profile generation module 115 to produce the cognitive and/or sensory assessment of the subject indicative of the progression of or vulnerability to the neurological or neuropsychiatric disorder and/or treatment he/she is undergoing for the disorder. In such exemplary implementations, the system 100 can use environmental stimuli (e.g., light, sounds, smells, tastes, and/or tactile contacts) that are presently available in the subject's surroundings. In such examples, the system 100 can be embodied on a single computing device, e.g., where the module 110 is configured to receive behavioral responses from the subject and/or record physiological data via inputs of the device.

Other examples of the disclosed systems and methods are provided in PCT Patent Application PCT/US13/62491, entitled "SYSTEMS AND METHODS FOR SENSORY AND COGNITIVE PROFILING," filed Sep. 27, 2013, of which the entire contents are incorporated by reference for all purposes as part of the disclosure of this patent document.

In some implementations of the disclosed technology, the physiological data acquisition module 110 can include a portable sensor device including an optimal configuration of electrophysiological signal detection electrodes frontally placed on the forehead of the subject to provide a cognitive and/or sensory assessment, e.g., related to the subject's vulnerability or pathological progression to a neurological or neuropsychiatric disorder or efficacy of a treatment to the disorder. Some examples of such systems are provided in PCT Patent Application PCT/US13/64892, entitled "CONFIGURATION AND SPATIAL PLACEMENT OF FRONTAL ELECTRODE SENSORS TO DETECT PHYSIOLOGICAL SIGNALS," filed Oct. 14, 2013, of which the entire contents are incorporated by reference for all purposes as part of the disclosure of this patent document.

In some examples, an exemplary portable electrophysiological sensor devices of the disclosed technology can include frontal EEG signal recording electrodes located on the subject's forehead for versatile, rapid, and non-obtrusive physiological data acquisition (e.g., including brain signal monitoring) that do not overlap with hair. For example, in some implementations, the exemplary physiological sensor devices are configured to a small size and can be formed with a variety of different materials (e.g., which can be tailored for specific applications), such that the devices may be easily applied, barely or not even felt by the user, or seen by others. For example, application and operation of such devices can be performed by a user, e.g., following simple instructions, without any need for technical expertise to apply or operate the device. This can significantly mitigate problems present in existing systems including the need of technical expertise for operation and lack of comfort and portability of sensor devices.

Figure 1E:
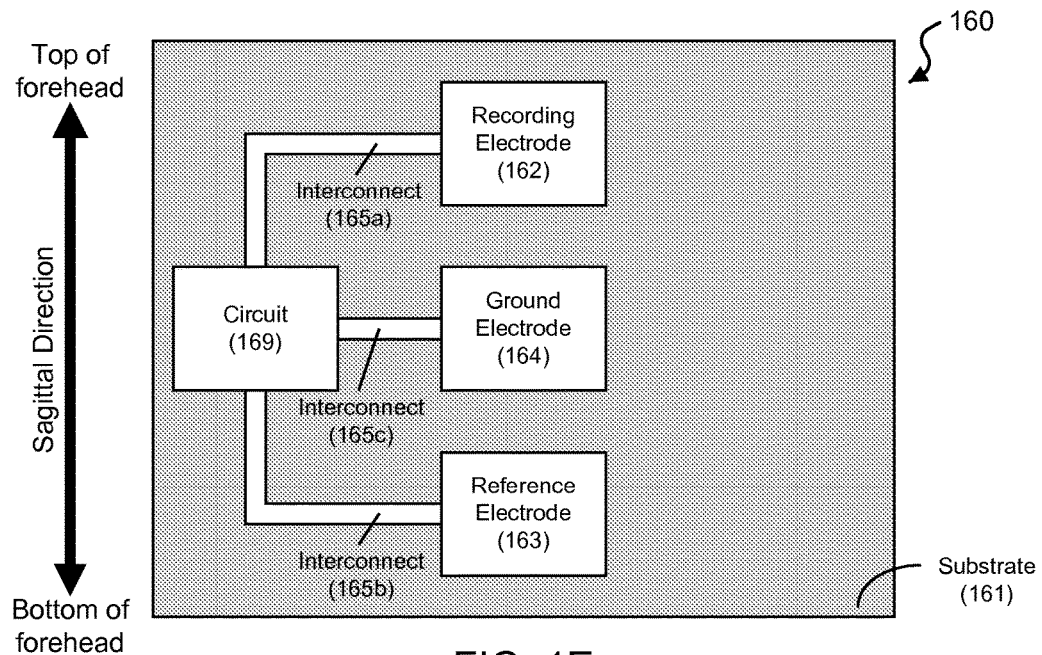
FIGS. 1E and 1F show block diagrams of an exemplary frontal electrode physiological sensor device of the disclosed technology.
Figure 1F:
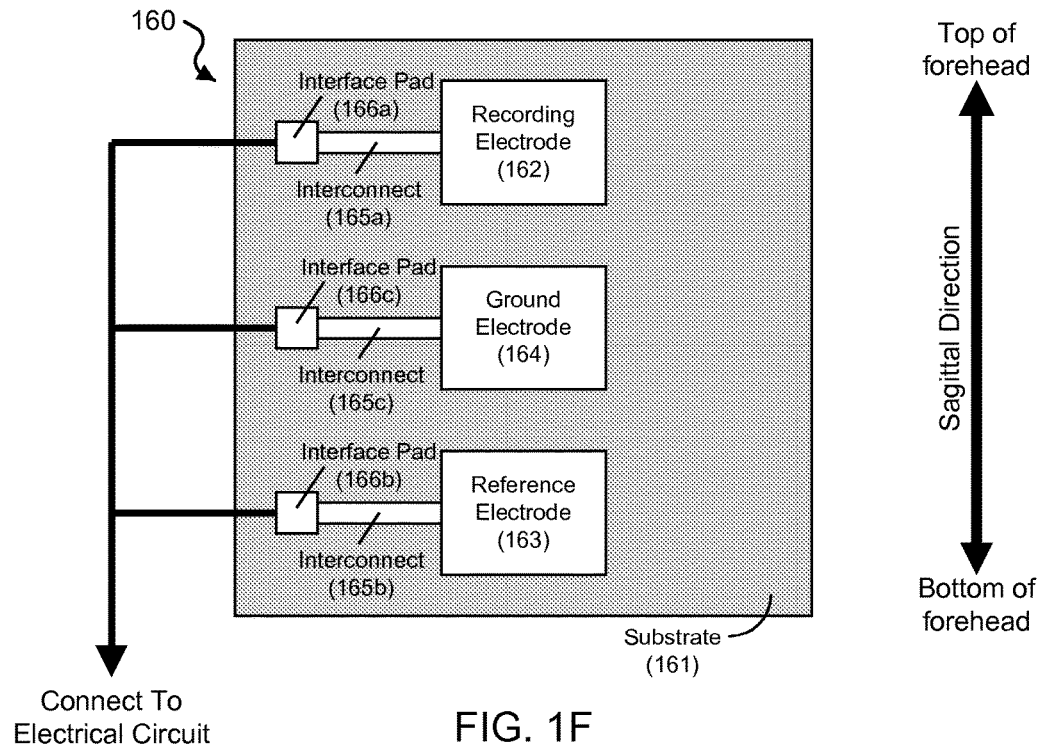

FIG. 1E shows a block diagram of an exemplary embodiment of a frontal electrode sensor device 160 capable to acquire electrophysiological signals from the frontal region of the head of a subject. The device 160 includes a substrate 161 of an electrically insulative material, which, in some device implementations, can be made of a mechanically flexible material. In some examples, the substrate 161 can include polydimethylsiloxane (PDMS), thin polyurethane with acrylic adhesive, or polyvinyl alcohol (PVA), among others. The frontal electrode sensor device 160 includes a three-electrode configuration, including a recording electrode 162, a reference electrode 163, and a ground electrode 164 configured between the recording electrode 162 and the reference electrode 163 on the basal side of the substrate 161 (e.g., the detection side of the device 160 that is in contact with the skin of the user). The electrodes of the device 160 are configured along a sagittal direction in the frontal region such that the recording electrode 162 is positioned posteriorly to the ground electrode 164, which is positioned posteriorly to the reference electrode 163. The ground electrode 164 is positioned at least partially between the recording electrode 162 and the reference electrode 163 on the substrate 161. This recording-ground-reference electrode arrangement on the frontal region of the user's head or forehead region can minimize the overall footprint of the electrodes of the frontal electrode sensor device 160, a significant benefit for such sensor devices. This recording-ground-reference electrode arrangement also provides good signal isolation between the recording electrode and the reference electrode, thus enabling more sensitive and high quality signal recording operation. The general alignment of the electrodes in the sagittal direction, rather than the horizontal direction that is perpendicular to the sagittal direction, is a notable feature of this recording-ground-reference electrode arrangement and can provide beneficial sensing operations with respect to acquiring various cognitive/psychological state signals with desired accuracy.

In some embodiments of the device 160, for example, the recording electrode 162, the ground electrode 164, and the reference electrode 163 are linearly arranged on the substrate 161. For example, the arrangements of the three electrodes can be aligned in a substantially straight line along the sagittal direction, with the recording electrode. In other embodiments of the device 160, for example, the three electrodes can be arranged in a nonlinear alignment that includes the recording electrode 162 positioned posteriorly to the ground electrode 164 that is positioned posteriorly to the reference electrode 163, with the ground electrode 164 at least partially between the recording electrode 162 and the reference electrode 163 on the substrate 161.

The frontal electrode sensor device 160 is operable to acquire electrophysiological data when electrically coupled to an electrical circuit. In the exemplary embodiment shown in FIG. 1A, the frontal electrode sensor device 160 includes an electrical circuit 169 on the substrate 161 electrically coupled to the recording electrode 162, the reference electrode 163, and the ground electrode 164 via individual electrical interconnects 165a, 165b, and 165c, respectively. In some embodiments, for example, the electrical circuit 169 can include a transmitter unit in electrical communication with each of the electrodes 162, 163, and 164, e.g., via the electrically conductive conduits 165a, 165b, and 165c, respectively. In this embodiment, the device 160 can record the physiological signals and transmit the recorded physiological signals to a remote electrical signal processing unit, e.g., such as an amplifier, and/or a computer system. Also, for example, the electrical circuit 169 can include a power supply module electrically coupled to the transmitter unit to provide electrical power to the transmitter unit.

In some embodiments, for example, as shown in FIG. 1B, the frontal electrode sensor device 160 can include electrically conductive interface (contact) pads 166a, 166b, and 166c coupled to the interconnects 165a, 165b, and 165c, respectively, to provide a conductive surface to electrically interface an external electrical circuit to the electrodes 162, 163, and 164 of the device 160. For example, the external electrical circuit can be an electrical signal processing unit, e.g., such as a signal amplifier, and/or a computer system.

For example, the acquired recording, reference, and ground signals are received by the signal processing unit that processes the acquired signals in a differential amplifier to amplify the difference between the recording and reference electrophysiological signals. The ground signals recorded by the device 160 (via the ground electrode 164) can be connected to the ground channel of the exemplary differential amplifier, e.g., to synchronize the signal parameters between the device 160 and the amplifier. For example, the ground electrode 164 can minimize leakage currents that may flow through the subjects via the recording system, and thus decrease any artifacts. For example, the ground electrode 164, when electrically coupled to an electrical circuit (e.g., such as the external electrical circuit), need not be connected to the ground of the electrical circuit. Alternative roles of the ground electrode can include serving as an electrode for actively canceling interference. For example, the ground electrode can be electrically connected to a "driven right leg" feedback circuit, e.g., which is used in some biological signal amplification systems that measure very small electrical signals emitted by the body (e.g., EEG, EMG, ECG). For example, the frontal electrode sensor device 160 can acquire referential recordings of electrophysiological signals at the frontal region. The position of the reference electrode 163, as well as its spacing with respect to the recording electrode 162 (or, in some implementations, other recording electrodes in addition to the recording electrode 162) is important, since the recordings of interest will be determined by a comparison of the activity recorded by the recording electrode 162 with respect to the activity recorded by the reference electrode 163. For example, if such signals were the same, then the detected signal reading would be zero. From this perspective, for example, one could position the recording electrode 162 at a site that will allow for detection of the physiological signal of interest and position the reference electrode 163 at a substantial distance away from it at a site that will not capture the physiological signal of interest (or show a significant reduction of the signal of interest). However, this presents a challenge that becomes greater when it is important to minimize the footprint of the device 160 (e.g., the occupied spatial area or "real estate" by the whole array of electrodes) on the forehead. For example, in the examples shown in FIGS. 1A and 1B, the electrodes 162, 163, and 164 are positioned and spaced in such a manner that the signals captured are significantly different, and thereby relevant, as well as occupy a minimal total area occupied by electrodes 162, 163, and 164. Methods are described in this patent document to determine optimal configurations of location and spacing are complex and can integrate psychological, neurophysiological and engineering principles. In the example shown in FIGS. 1A and 1B, the position of the reference electrode 163 is located in a substantially linear alignment with respect to the recording electrode 162, and both electrodes 162 and 163 and the ground electrode 164 are also arranged on a mid-sagittal line through the center of the frontal region, in this example. The signal-processed signals are provided as physiological data, which can subsequently be processed to provide a cognitive and/or sensory profile.

In some implementations, the device 160 can be configured as an epidermal electronics physiological sensor device that can be worn directly on skin or a wearable item in contact with the frontal region. In some implementations, for example, the device 160 can include an additional electrically insulative layer or layers, e.g., configured on the apical side of the device 160 (e.g., the non-detection side, not in contact with the skin of the user). The additional layer(s) can provide further support for the device 160. In some examples, the additional layer(s) can include various artistic designs, such that, when worn by the user directly on the user's skin, the device 160 can also serve as a (temporary) tattoo.

Within the framework of the disclosed methods, an application program that can be implemented on a computer system of the disclosed technology can be configured such that the user of the application (e.g., operator of the system) will interact with the client application (e.g., stimulus presentation and data acquisition program), which can be presented to the user via a graphical user interface (GUI). In some implementations of the application, the program can instruct the user on how to place the EEG recording electrodes on the subject's head to simplify the recording process, e.g., including instructions for placement of a full EEG cap (e.g., using rigid electrodes) or placement of a frontal electrodes based sensor device (e.g., using flexible electronics). For example, this type of interaction between the computer implemented application and the user can expedite the overall process and prevent potential issues from arising, such as "cross-talk" between multiple electrode channels.

Figure 1G:
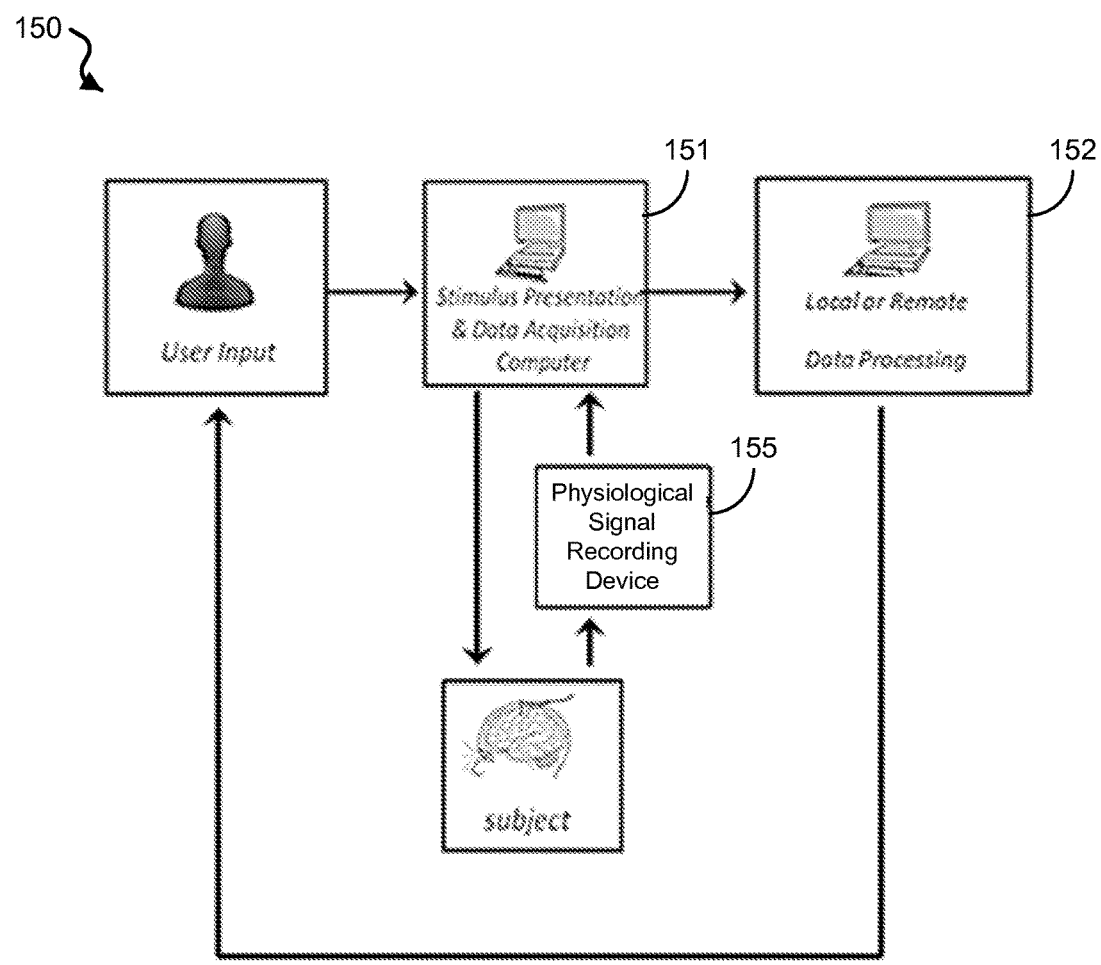
FIG. 1G shows a diagram of another exemplary system of the disclosed technology for characterizing pathology and/or vulnerability of subjects to a neurological or neuropsychiatric disorder and/or assessing treatments for such disorders.

FIG. 1G shows a diagram of a system 150 for characterizing pathology and/or vulnerability of subjects to a neurological or neuropsychiatric disorder and/or assessing treatments for such disorders. For example, the system 150 is operable to implement the exemplary application program. The system 150 includes a stimulus presentation and data acquisition computer 151 to interact with a subject and an operator, and collect physiological signal data from the subject via a physiological signal recording device 155 (e.g., such as the device 160 or rigid electrode based recording device). For example, the operator can provide input into the stimulus presentation and data acquisition computer 151 to initiate an assessment of the subject (e.g., including a vulnerability and/or progressive pathology assessment or a treatment efficacy assessment for a neurological or neuropsychiatric disorder). The system 150 includes a data processing computer 152, which can be a local computer with respect to the computer 151 (e.g., and in some examples, be the same computer as 151), or the computer 152 can be a remote computer or network of computer systems, e.g. in communication with the computer 151, for example, via the Internet. For example, the data processing computer 152 is configured to process the collected physiological data and generate an assessment depicting a level of vulnerability to or progressive pathology of the neurological or neuropsychiatric disorder and/or efficacy of a treatment for the disorder. For example, the generated assessment can provide the user (e.g., operator and/or subject) with an information set that can be used as input into the stimulus presentation and data acquisition program implemented by the computer 151. In some implementations, the operator can select the profile category on the stimulus presentation and data acquisition computer 151, e.g., presented to the operator via the GUI, prior to initiating the stimulation presentation and data acquisition processes. As shown in FIG. 1G, the stimulus presentation module and the data acquisition module can be configured in the computer 151 to run in parallel and communicate information to each other, e.g., such as coordinating the timing of stimulus onset. Sensory stimulation (e.g., auditory and/or visual, etc.) can be presented to the subject from the computer 151 while the physiological signals (e.g., EEG) are recorded. The application program implemented by the system 150 can allow for, for example, the users to be able to choose the stimulus presentation paradigm, the data acquisition device, and the signal processing technique(s).

Exemplary Implementations of the Disclosed Methods and Systems for Profiling Neuropathologies and Disorders Described are exemplary implementations of the disclosed systems and methods for providing a cognitive and/or sensory assessment of a subject (or a group) indicative of one or more aspects of cognitive or sensory functions, e.g., which can be used for diagnosis or evaluation of vulnerability and pathological progression to a neurological or neuropsychiatric disorder, or assessment of efficacy of treatment (e.g., drug development) to the disorder. The subjects include human and non-human primates.

In the described examples, specific stimuli sets are presented while recording EEG signals from the subject to elicit event-related potentials of interest, as well as correlated neural frequency oscillations. The exemplary ERPs used in the exemplary implementations include, but are not limited to, the P300 and the mismatched negativity. Other exemplary ERPs that can be implemented to provide an exemplary cognitive-sensory profile using the disclosed technology include, but are not limited to, the N400 as well as ERP responses associated with the cognitive processing of a feeling/notion of reward. The disclosed cognitive and/or sensory profile generation methods and systems can be used to measure a subject's brain markers, and in addition, evaluate and transform this information into purposeful data that characterizes the subject's vulnerability to or progressive pathology in a neurological or neuropsychiatric disorder, and thereby providing an assessment profile of the disorder. For example, in applications related to the use of a non-human primate animal model, the exemplary implementations include electrophysiological measurements performed under multiple physiological treatments/conditions, which can form the basis of a functional and usable animal model for neurological and neuropsychiatric disorders, e.g., including schizophrenia and Alzheimer's disease, among others.

Schizophrenia is a neuropsychiatric disorder that affects approximately one percent of the human population, which in the United States, accounts for approximately 3 million persons. Schizophrenia can be associated with symptoms such as hallucinations, paranoia, disorganized thinking, flat affect, and poor executive functioning. Conventional diagnosis and pathological evaluation procedures are based on observed behavior and reported experiences. For example, a patient may report symptoms such as auditory hallucinations, delusions, and suicidal thoughts. As in other neuropsychiatric disorders, while clinical observation and self-reporting can be beneficial, a more objective method for diagnosis and pathological evaluation are needed. For example, a specific case of a mental disorder, such as schizophrenia, may or may not exhibit many of its stereotypical symptoms at the time of diagnosis, but may become present at a later time, which further adds to the complexity of the diagnostic process.

Some suggest that the disorder may at least partially result from dysfunctions in the gamma-Aminobutyric acid (GABA) and glutamate neurotransmitter systems. For example, it has been found that acute sub-anesthetic doses of the N-methyl-D-aspartate (NMDA) receptor antagonist ketamine can induce perceptual, cognitive, and neural deficiencies typical to those present in schizophrenia. Several antipsychotic drugs since the 1950s have been manufactured to treat this neuropsychiatric disorder, many of which target these specific neurotransmitter systems. However, most drugs do not adequately address the disorder itself and its symptoms and can involve adverse side effects, e.g., such as cognitive dulling, dyskinesia (involuntary body movements), or agranulocytosis (low white blood cell count). Also, for example, current second generation antipsychotic drugs have been found to have vast limitations in their effectiveness in patients with chronic schizophrenia and do not differ significantly in terms of effectiveness with conventional, first generation drugs.

Both pharmacological research and patient care (e.g., including diagnostic, vulnerability assessment and monitoring of progressive pathology) currently lack novel reliable and effective ways to relate assessable brain markers (derived from brain physiology) with neuropsychiatric disorders of interest, building more objective correlations that go beyond behavioral assessment. For example, in patients with Alzheimer's disease, as well as suffering from schizophrenia, the amplitude of the mismatch negativity ERP (associated with echoic memory and variance detection) can be attenuated, e.g., indicating a deficit in cognitive updating, and thus suggesting cognitive decline, decreased memory-trace duration, and/or affected auditory discrimination. Also, for example, those affected by Alzheimer's disease present decreased amplitudes and increased latencies of the P300 ERP (a brain marker associated with modulation of attention) as compared to healthy subjects.

Mismatch Negativity

Mismatch negativity (MMN) is an ERP modulation that is an automatic, pre-attentive index of functioning sensory memory processing at the level of auditory sensory cortex. MMN can be elicited by auditory and visual stimuli. MMN is thought to reflect pre-attentive detection of a deviant stimulus and can be calculated as the difference wave between the responses to deviants (e.g., infrequent) and to standard (e.g., frequent) stimuli in an 'oddball' paradigm. For example, the MMN usually occurs between 100 and 250 ms after the onset of the deviant stimulus, with maximal voltages over frontal and central EEG scalp locations. It can be elicited by both basic violations of a pattern (e.g., violating a pattern of a given pitch/frequency by presenting a stimulus of a higher or lower pitch) as well as more abstract deviancies (e.g., violating a pattern of "staircasing" frequencies by presenting a pitch equal or lower than the preceding stimulus).

MMN can be correlated with a wide range of neurological and neuropsychiatric disorders. For example, scientific studies on patients suffering from a variety of mental disorders, e.g., including schizophrenia, Alzheimer's disease, and autism spectrum disorder (ASD), have systematically reported that these patient show a decreased ability to detect novel stimuli than healthy subjects. Consistent with this behavior deficit, the amplitude of the MMN is reduced, and thus the MMN can be treated as a marker of either progressive pathology or vulnerability for these disorders.

Figure 2:
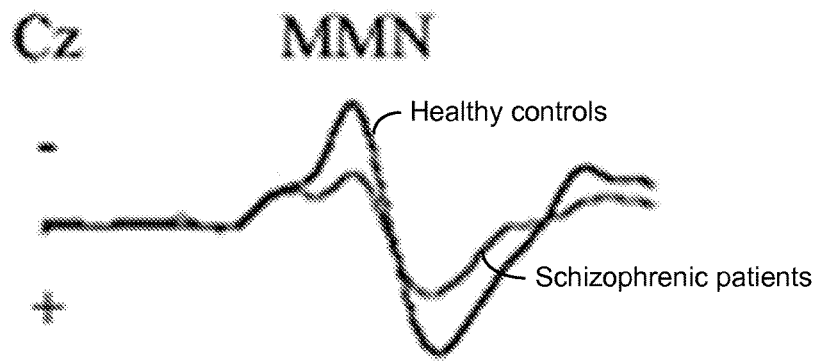
FIG. 2 shows a data plot illustrating the mismatch negativity ERP as a marker of progressive pathology for schizophrenia.

For example, schizophrenic patients often exhibit a deficiency in MMN generation, suggesting an impairment in pre-attentive processing and in cognitive updating. MMN has been used as a marker for progress pathology for schizophrenia. FIG. 2 shows a data plot with exemplary results of a study comparing the MMN of healthy patients (controls) with patients with schizophrenia using a single electrode (Cz), which demonstrates a significant reduction of the MMN among schizophrenia patients. For example, the measurement of the MMN can offer physicians/clinicians a reliable biological marker of post-onset progressive cognitive decline in schizophrenia, allowing them to more accurately diagnosis patients and chart the spread of the disorder.

P300

The P300 can be characterized by a positive-going electrical response between 300 and 800 ms, with a central-parietal maxima scalp distribution. The P300 is inversely correlated with an item's subjective probability of occurrence. For example, the P300 has been used in visual target detection tasks, where the target elicits higher amplitude P300s than the other items.

The P300 is an event related potential that can be elicited by auditory and visual stimuli, often within an oddball paradigm. Although it reflects the indexing of deviant stimuli, like the MMN, the P300 distinguishes itself from the MMN by indicating the redirection of attention to a deviant stimulus. It thereby indexes stimulus significance and it is maximal to task-relevant and/or attended stimuli. The amplitude of the P300 is typically maximal over medial central and parietal EEG scalp locations, and occurs between approximately 300 and 1000 ms after deviant stimulus onset. For example, significant decreases of the P300 response have been associated with various neuropsychiatric disorders that include attention and cognitive updating deficits, such as Alzheimer's disease and schizophrenia, amongst others, with smaller P300 amplitudes compared to those of healthy controls. Moreover, for example, deficits in P300 generation have been shown to be present in high-risk persons, who can be defined as individuals with relatives who suffer from the disorder.

Figure 3:
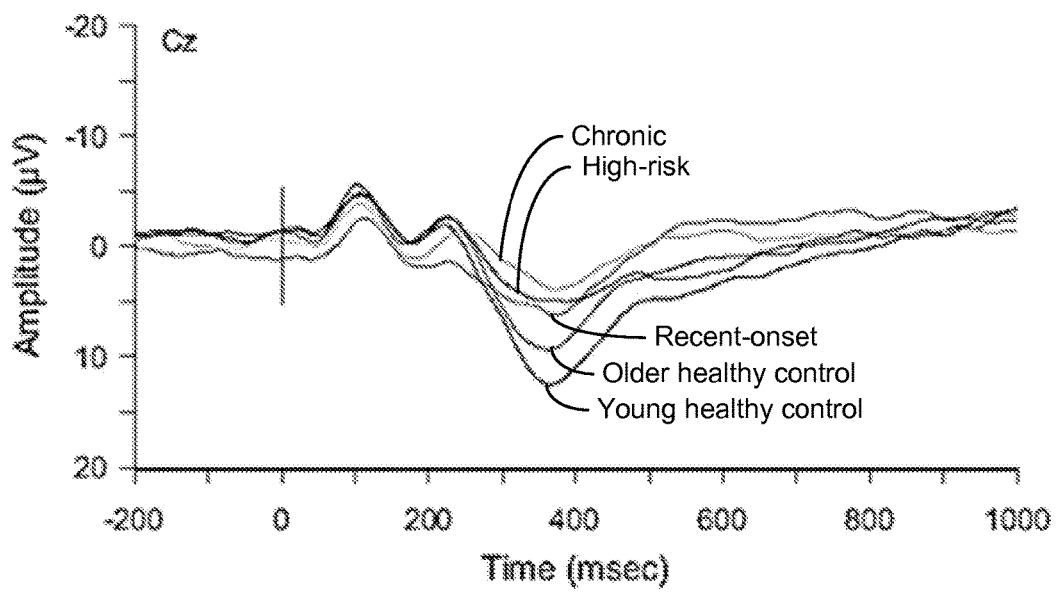
FIG. 3 shows a data plot illustrating the P300 ERP as a marker of vulnerability for schizophrenia.

FIG. 3 shows a data plot with exemplary results of a study comparing the P300 of various groups of subjects including young healthy patients and older healthy patients (controls) with high-risk, recent-onset, and chronic patients with schizophrenia using a single electrode (Cz), which demonstrates a significant reduction of the P300 among schizophrenia patients. For example, as shown in the data plot of FIG. 3, individuals with a family history of schizophrenia but still clinically unaffected (e.g., considered "high-risk" patients) also exhibit reduced P300 amplitudes. Moreover, the data plot reveals a distinct gradient of P300 amplitudes, well correlated with the risk of, or existent pathology between the investigated population groups. The disclosed technology can be used to index an individual's (or group's) vulnerability to a neuro-disorder and/or -pathology, e.g., such as schizophrenia, which may allow for the individual to obtain earlier and/or potentially preventative treatments/therapies, e.g., when such exist and are proven effective.

I. Exemplary Implementations with MMN and P300 ERPs in Human Subjects for Evaluation of Vulnerability and Progressive Pathology of Neuropsychiatric Disorders I.1. Exemplary Stimuli Presentation Structure Five adult male subjects (e.g., between 20 and 36 years old) were evaluated in exemplary implementations of the disclosed technology to assess vulnerability and/or progression of pathology to neuropsychiatric disorders.

Figure 4:
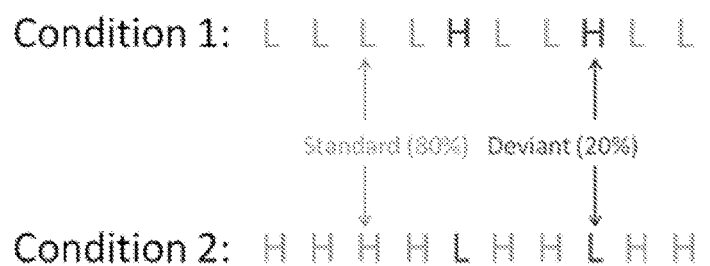
FIG. 4 shows a diagram illustrating an exemplary intensity (decibel level) oddball paradigm for auditory stimulus presentation.

The exemplary stimuli presentation structure included a passive auditory intensity oddball paradigm to present different intensity tones to the human subjects, who each sat in an isolated, dimly lit room during the implementations. For example, the auditory stimuli included 100 ms (e.g., 10 ms rise/fall) pure sinusoidal tones (e.g., 1500 Hz) of either a low or a high intensity. Frequent (standard) and infrequent (deviant) stimuli were presented 80% and 20% of the time, respectively, as shown in FIG. 4. FIG. 4 shows a diagram illustrating an exemplary intensity (decibel level) oddball paradigm for auditory stimulus presentation. The inter-stimulus interval was 700 ms. For example, twelve hundred standard and three hundred deviant stimuli were presented in each exemplary recording session. For example, both high-deviant (e.g., low-standard) and low-deviant (e.g., high-standard) conditions were used, e.g., to allow comparison of the responses to identical stimuli (e.g., low or high) in different contexts (e.g., standard or deviant).

The exemplary stimulus presentation paradigm that was used to control the presentation of stimuli in this example was programmed using Cogent 2000. For example, other software packages that can be used include, but are not limited to, Psychtoolbox, E-Prime, Presentation, and Qt. The tones were presented to the human subjects using a speaker. The exemplary human subjects were asked to maintain central fixation, e.g., to minimize movement artifacts. For example, the fixation target was a red circle (e.g., 1 degree in diameter) on a black background presented using a 21 inch CRT monitor at 40 cm distance from the subject. The target appeared before the beginning of auditory stimulus presentation and remained visible for the entire duration of the recording session. For example, two methods were used to create the exemplary red, central fixation dot and the blue square stimulus. For the exemplary fixation dot, for example, a computer implemented process (e.g., created using a MATLAB script) was used to create a black background image (e.g., red gun equal to 0; green gun equal to 0; blue gun equal to 0) with a height and width of 350 pixels. Then, the exemplary script ran a nested for-loop using the standard equation of a circle to alter pixels within a seven pixels length radius to red by changing the image's red gun to 255, the green gun to 0, and the blue gun to 0. For the exemplary blue square stimulus, imaging software was used to create a 157×157 pixel sized image, whose red gun was equal 0, green was equal 0, and blue was equal 255. The exemplary red, central fixation dot was used to help subjects maintain fixation throughout the recording sessions.

The exemplary computer implemented process was used to configure the display, a Cogent 2000 log file, parallel port, and sound card. Then, the exemplary computer implemented process was used to load in the auditory stimuli (e.g., low and high tones) and the visual stimuli (e.g., fixation dot and blue square) into memory buffers. For example, in order to create a greater perception of deviancy, the exemplary process did not present two or more deviant stimuli consecutively. For example, this was achieved by creating presentation order comprised of an array of "1's" and "2's." For example, the "1's" represented standard stimuli, and the "2's" represented deviant stimuli. In some implementations, for example, the aforementioned steps can be executed prior to stimulus presentation in order to reduce computational load and increase latency precision.

For example, within the presentation for-loop (of the exemplary MATLAB script of the exemplary computer implemented process to produce the fixation target), the fixation dot was presented and remained visible to the subject throughout the entire block. Then, the loop iterated down the presentation order. When it encountered a "1", the exemplary computer implemented process would first send an event marker/trigger to the physiological data acquisition system (e.g., EEG recording computer), followed immediately by the presentation of the standard stimulus (e.g., low tone for condition 1; high tone for condition 2). Likewise, when it encountered a "2", the exemplary computer implemented process would first send an event marker/trigger to the exemplary EEG recording computer, followed immediately by the presentation of the deviant stimulus (e.g., high tone for condition 1; low tone for condition 2). The event marker/trigger indicated which stimulus (e.g., low or high) was presented. For example, each auditory stimulus was followed by an inter-stimulus interval (ISI) of 700 ms. For example, in the exemplary implementations, the fixation target was merely an aid to help minimize ocular movement, and as such fixation was not quantified.

I.2. Exemplary EEG Data Collection/Recordings

In some implementations, for example, a traditional EEG system with rigid electrodes was used to acquire brain waves. For example, EEG scalp recordings were acquired with the Vision Recorder software using a BrainAmpMR system. A 64-channel EEG cap BrainCap MR was used with AgCl electrodes for human subject data collection (e.g., PCB Ribbon Cable for BrainCap-MR with 5 k resistors; BrainCap MR Box 1.2; sintered ring electrodes with 1.5 mm touchproof safety socket termination and 120 cm heavy-duty leadwire).

The human subjects were seated in a chair in the recording chamber and began the electroencephalography capping process. For example, this process involved placing the EEG cap on the subject's head and securing it with an elastic chin strap. In some examples, either a 56 cm or a 58 cm diameter cap was used, based on the estimated size of the subject's head. Next, Signa electrode gel was injected using a curved, plastic syringe under each of the cap's electrodes to create a conductive bridge between the electrode itself and the subject's scalp. We also used wooden Q-tips to massage the gel in order to build a stronger conductance by lowering the impedance. Also, for example, wooden Q-tips were used to massage the gel in order to build a stronger conductance by lowering the impedance. For example, use of this technique lowered the impedance levels to <5 kΩ for each electrode, e.g., including the ground and reference.

Before starting the exemplary implementation using EEG recordings, subjects were seated in front of the presentation monitor and audio speaker and asked to maintain visual fixation on the exemplary red, central fixation dot throughout the duration of the entire implementation and restrict their motor movements as much as possible to prevent motion artifacts in the neurophysiological data. For example, to emphasize these points, the subjects were shown the online recording of their raw brain waves, which demonstrated to them what happens to the data when they frequently blink and/or clench their jaw. Lastly, prior to beginning the implementation, for example, the recording room's lights were turned off completely, windows were blacked out, and cracks were sealed to prevent exterior light from entering.

I.3. Exemplary EEG Data Analysis

The exemplary EEG data was analyzed using Analyzer 2.0 software. In the exemplary implementations, the same analyses were applied to data from humans and monkeys. For example, the analysis procedure included first re-referencing the data sets from the original recording references to identical posterior occipital channels, as a new comparable reference between species (e.g., human: Oz, O1, O2, PO7, PO8, P7, P8; rhesus macaque: Oz, O1, O2, P3, P4). This was followed by band-pass filtering (e.g., Low Cutoff: 0.1 Hz, High Cutoff: 50 Hz) and changing the sampling rate from 1000 Hz to 250 Hz based on spline interpolation. For example, in order to avoid analysis artifacts stemming from differences in sample size, the exemplary data sets were first segmented relative to the deviant markers position (e.g., start: −1000 ms, end: 600 ms), so that it would include all deviant trials (e.g., N=300) and only the standard trials (e.g., N=300) immediately preceding the deviants. Subsequently, for example, the resulting epochs were segmented relative to either the deviant or the standard marker positions (e.g., start: −200 ms, end: 600 ms) identifying the relevant deviant and standard epochs. For both standard and deviant epochs, a baseline correction (e.g., start: −200 ms, end: 0 ms) was applied, a multiple features artifact rejection tool was applied (e.g., applied to all channels; maximal allowed voltage step: 50 µV/ms; maximal allowed difference of values in intervals: 200 µV; lowest allowed activity in intervals: 0.5 µV). The ERP (average) was then calculated for each channel and condition (e.g., high-standard, low-standard, high-deviant and low-deviant). For example, difference waves (e.g., deviant minus standard) were calculated for both conditions (e.g., low-deviant minus low-standard and high-deviant minus high-standard), and subsequently the low and high difference waves were averaged to yield the MMN component, and the low and high responses to deviants were averaged to yield the P3 component.

I.4. Identification of Human ERPs

In the exemplary implementations, the exemplary MMN and P3 ERP components were identified in humans using established criteria that employed the same testing paradigm (e.g., oddball paradigm where the MMN is the difference wave of deviant minus standard stimuli, and the P3 is observed on deviant stimulus trials), and the timing, electrode location, voltage scalp distribution and neural generators were ascertained for these ERP components. For example, after identifying the MMN, a 40 ms window was established around the peak amplitude in the average ERP wave. This exemplary time-window was used to extract peak amplitude values per subject from single trials. For example, these values were then used for statistical analysis in a 2-way repeated measures ANOVA (e.g., factor 1: standard vs. deviant; factor 2: high vs. low). The P3 component was investigated in the averaged response to low and high deviants. Similarly, for example, after identifying the P3 component, a 40 milliseconds window was established around the peak amplitude in the ERP wave, and that window was used to extract the mean amplitude values from single trials. For example, the statistical significance for a P3 response was calculated using a t-test.

I.5. Exemplary EEG Data Analysis Using Custom-Designed Program

In addition to calculating the MMN and P300 components using an existing software package (e.g., BrainVision Analyzer 2.0), the exemplary implementations also included determining the MMN and P300 components using an exemplary custom-designed computer implemented analysis process (e.g., programmed in MATLAB script) to process the MMN and P300 data to create the ERP waveforms. The exemplary custom-designed computer implemented program can be implemented to automatically process the data (e.g., performing signal processing steps such as filtering, channel removal, re-sampling, etc.), calculate the MMN difference wave ERP, calculate the P300 ERP, and perform statistical analyses on the given data, all with only a few guided mouse clicks. For example, using existing techniques, the time needed for a typical ERP pre-processing and analysis can range from several hours to several weeks. The exemplary custom-designed program can be implemented to process the data (e.g., such as that shown below) in an average of approximately 2-3 minutes. While the exemplary code was developed using MATLAB, its specific framework and analysis process could be implemented in other programming languages, e.g., including, but not limited to, C++ and Java. Moreover, its framework is not tied to the exemplary brain markers (e.g., MMN and P300) used in the exemplary implementations described herein, and can be applied to other brain markers, e.g., including, but not limited to the N400, as well as ERP responses associated with the cognitive processing of a feeling/notion of reward, and additional brain signals (e.g., such as neural frequency oscillations). Additionally, the flexibility of the exemplary custom-designed program can allow it to be applied on multiple platforms. For example, the exemplary computer implemented method could be run locally (e.g., on a user's laptop or desktop computer) or remotely (e.g., on a computer system or communication network accessible via the Internet (referred to as 'the cloud') that includes one or more remote computational processing devices (e.g., servers in the cloud)). In the following example, the computer implemented method uses MATLAB, e.g., because of its user friendly programming environment and built-in functionality to handle large data matrices.

Figure 5:
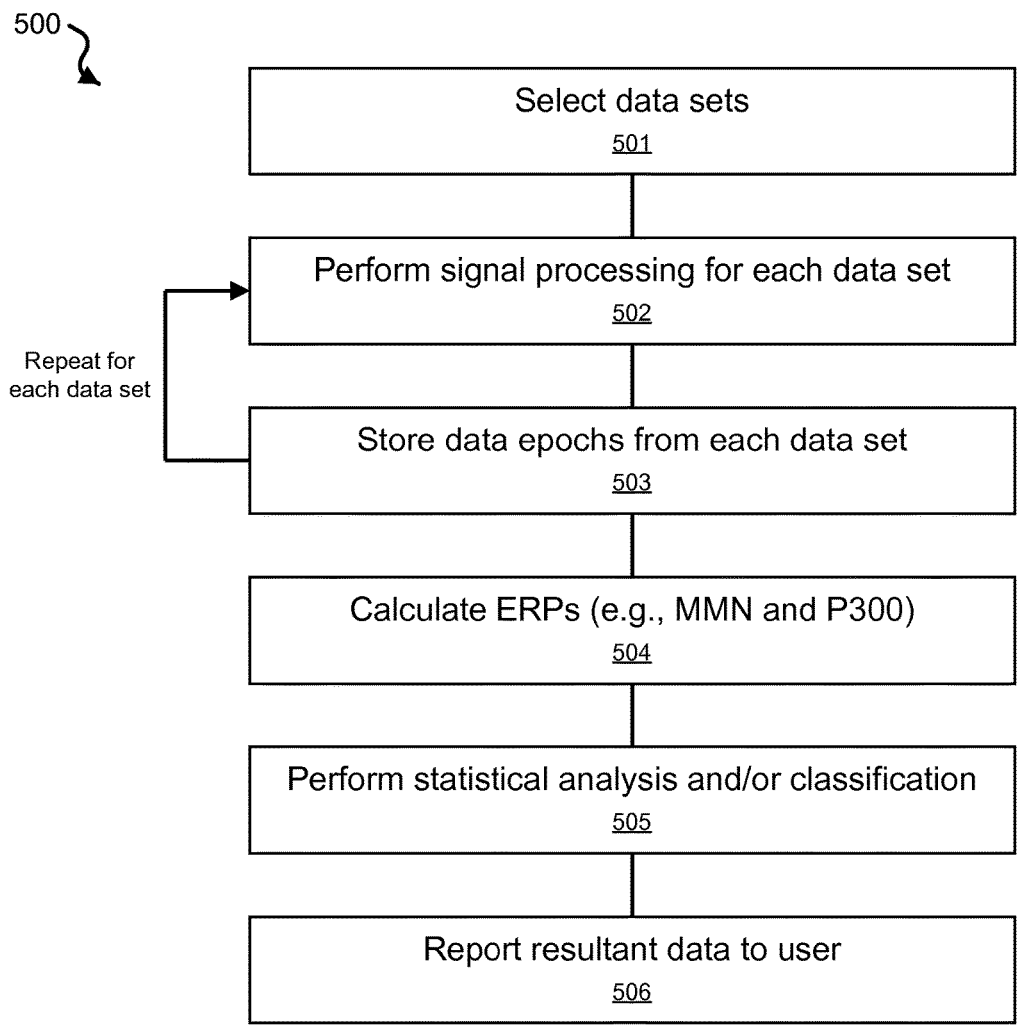
FIG. 5 shows a flow chart of the exemplary pre-processing and analysis process of the exemplary custom-designed computer implemented method.

FIG. 5 shows a flow chart of the exemplary pre-processing and analysis process 500 of the exemplary custom-designed computer implemented program. As previously mentioned, for example, this process, unlike existing techniques, is fully automated in order to aid the user in eliciting and measuring reliable brain markers, as well as expedite the process, which can be significantly beneficial in diagnosis and/or pathological evaluation and therapeutic drug development. Moreover, this exemplary automated process can allow individuals with little to no expertise in electrophysiological recording techniques to benefit from the disclosed technology and implement it within their own work.

The pre-processing and analysis process 500 includes a process 501 for the operator to select the data sets for use in the neurophysiological assessment of the subject, e.g., such as the physiological and/or behavioral data acquired from the subject by the exemplary data acquisition module during the exemplary stimulation presentation process. The pre-processing and analysis process 500 includes a process 502 to perform signal processing, e.g., including filtering, channel removal, re-sampling, etc., for each selected data set. The pre-processing and analysis process 500 includes a process 503 to store data epochs from each selected data set. The pre-processing and analysis process 500 includes a process 504 to calculate the ERPs (e.g., MMN, P300, etc.). The pre-processing and analysis process 500 includes a process 505 to perform statistical analysis and/or classification techniques of the disclosed technology to provide the vulnerability and/or progression of pathology assessment to the neurological or neuropsychiatric disorder. The pre-processing and analysis process 500 includes a process 506 to report and/or present the analyzed information set (e.g., including one or more quantitative values) associated with the selected profile category of the neurological or neuropsychiatric disorder assessment.

FIG. 6 shows an example of the exemplary pre-processing and analysis code (e.g., programmed in MATLAB script), using pseudo-code. As illustrated in FIG. 6, the exemplary code iterates through one or more data sets (e.g., which can include one or more physiological treatment conditions, e.g., ketamine and a potential therapeutic). In this example, the exemplary pre-processing and analysis code stores only one data set at a time in memory, e.g., in order to reduce memory and computational load. After a data set has been processed and its relevant data has been extracted, it is released from memory and replaced by a subsequent data set.

Figure 7:
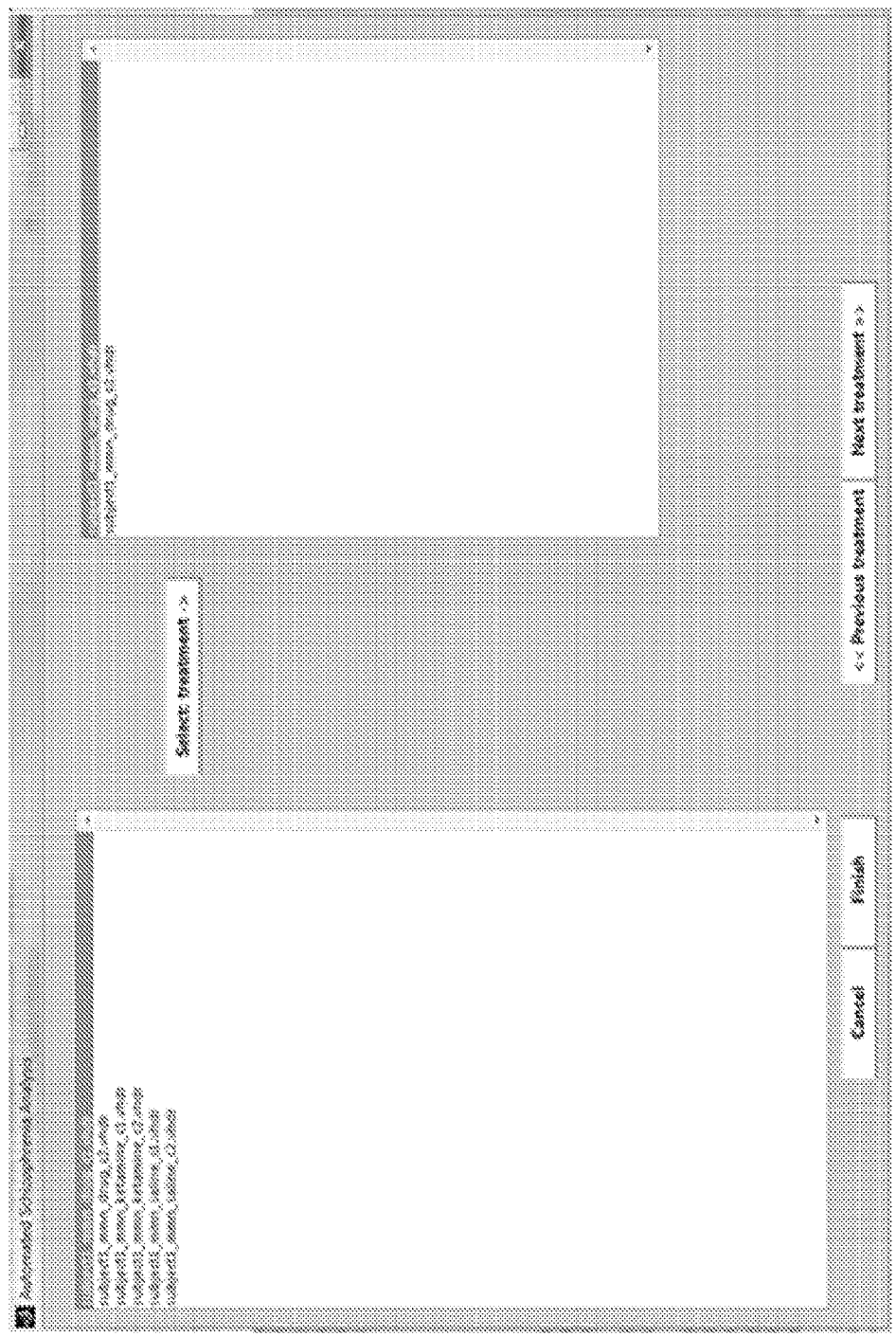
FIG. 7 shows an example of a graphic user interface (GUI) for an exemplary programming analysis process of the disclosed technology.

FIG. 7 shows a computer screenshot of an exemplary graphical user interface (GUI) of the exemplary programming analysis process. By using this exemplary interface, users are able to easily select which data set(s) they wish to analyze and can have the option of comparing data sets across multiple physiological treatments. For example, the left panel searches the current path for EEG files and lists their respective filenames. Using this panel, users can utilize their mouse to highlight which data sets they want to analyze and select them by clicking the "Select: treatment" button. This will 'move' the selected filenames to the right panel, indicating which files they have chosen. The user can subsequently press the "Next treatment" button to choose data sets for another physiological treatment. They can also press the "Previous treatment" button if they wish to go back and edit previous selections. Upon pressing the "Finish" button, the program will begin the automated analysis process and will conclude by outputting a results file to the user that can be subsequently saved.

To demonstrate the capability and accuracy of the exemplary systems and methods, including the custom-designed computer implemented data analysis program, the exemplary implementations included comparisons between exemplary results from the custom-designed analysis methods and the results using an existing software package (e.g., BrainVision Analyzer 2.0).

I.6. Characterization of MMN ERP in Humans

For example, using established characterizations of the timing and scalp topography of the MMN component in humans, the exemplary results revealed an MMN ERP with a duration from approximately 56 ms to 190 ms, with a peak amplitude of −1.83 µV at 104 ms ($F(1,1259)=97.12$; $p=0.000$), and a fronto-central and central scalp distribution.

Figure 8A:
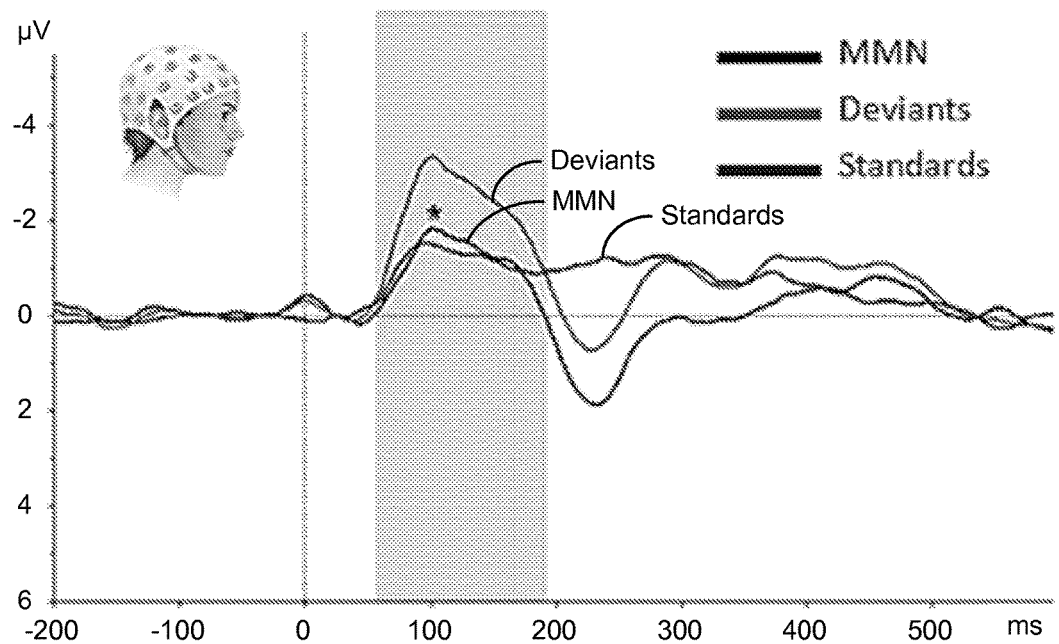
FIGS. 8A and 8B show data plots of exemplary ERP processing and analysis results using an exemplary dataset of the mismatch negativity ERP for human subjects.
Figure 8B:
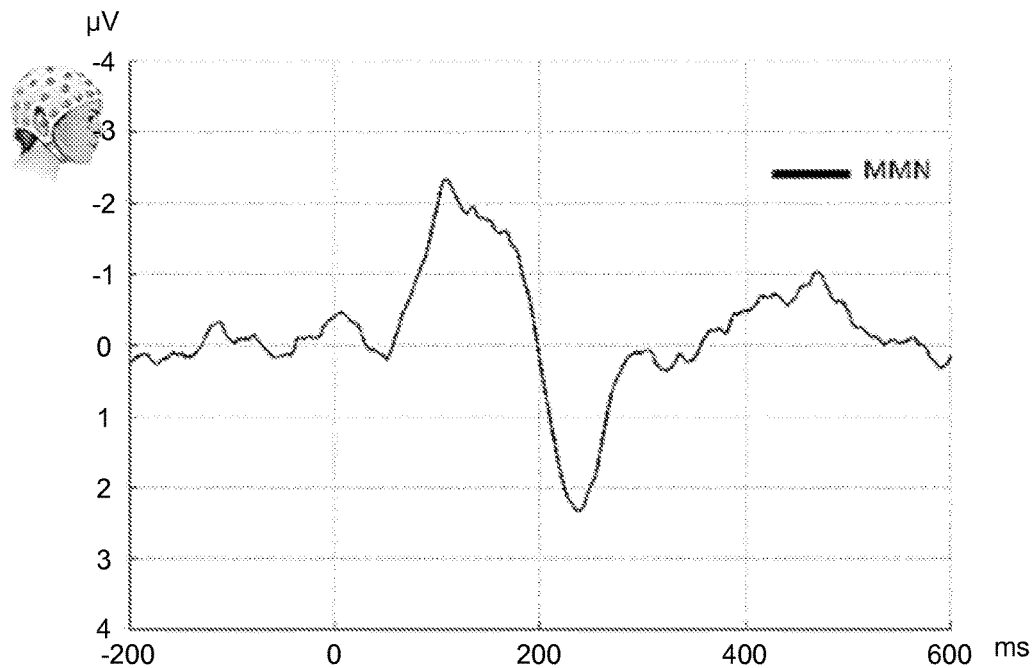

FIGS. 8A and 8B show data plots of exemplary ERP processing and analysis results for human subjects using an existing software tool (FIG. 8A) and the custom-designed program (e.g., using MATLAB script) (FIG. 8B) from an exemplary MMN data set. The data plots depict waveforms from the human subjects using the Cz electrode channel. For example, the data plots of FIGS. 8A and 8B illustrate the exemplary pattern of the MMN in healthy human subjects. The data plot in FIG. 8A includes the waveforms for the standards and deviants, and shows the strong discrimination between standards and deviants, as evidenced by the MMN, which is the difference of the deviant waveform minus the standard waveform. Likewise, in FIG. 8B, the exemplary ERP processing and data analysis using the exemplary custom-designed program yielded substantially the same results for the MMN waveform in the expected time interval.

I.7. Characterization of the P300 ERP in Humans

The P300 was investigated in the averaged response to low and high deviants. For example, using established characterizations of the timing and scalp topography of the P3 component in humans, the exemplary results revealed a P300 ERP with a duration from approximately 208 ms to 256 ms with a peak amplitude of 0.72 µV at 228 ms (t=3.54, p=0.000).

Figure 9A:
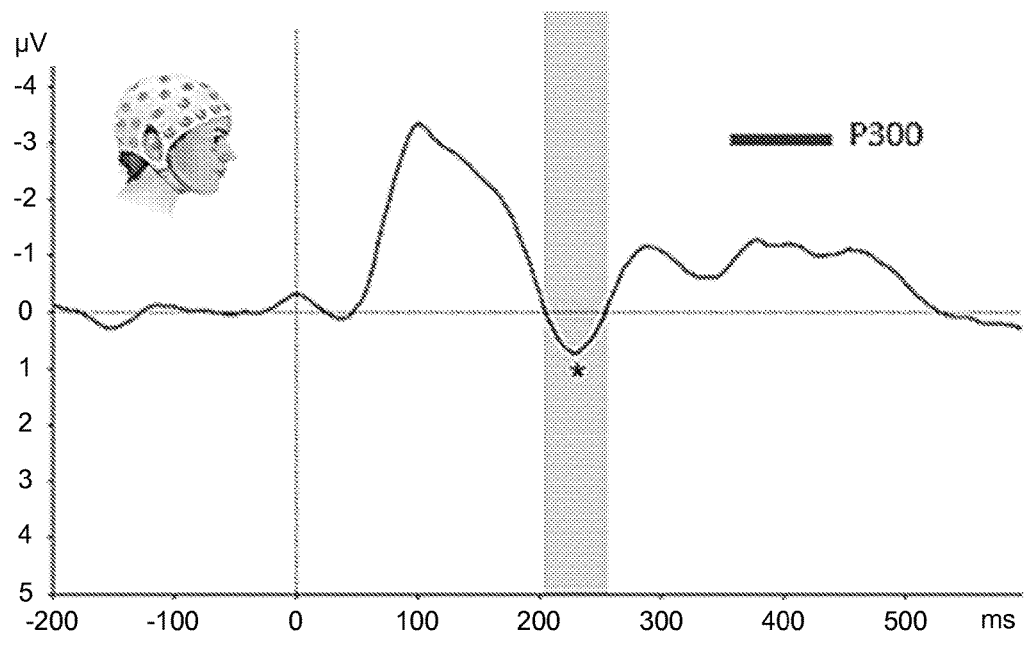
FIGS. 9A and 9B show data plots of exemplary ERP processing and analysis results using an exemplary dataset of the P300 ERP for human subjects.
Figure 9B:
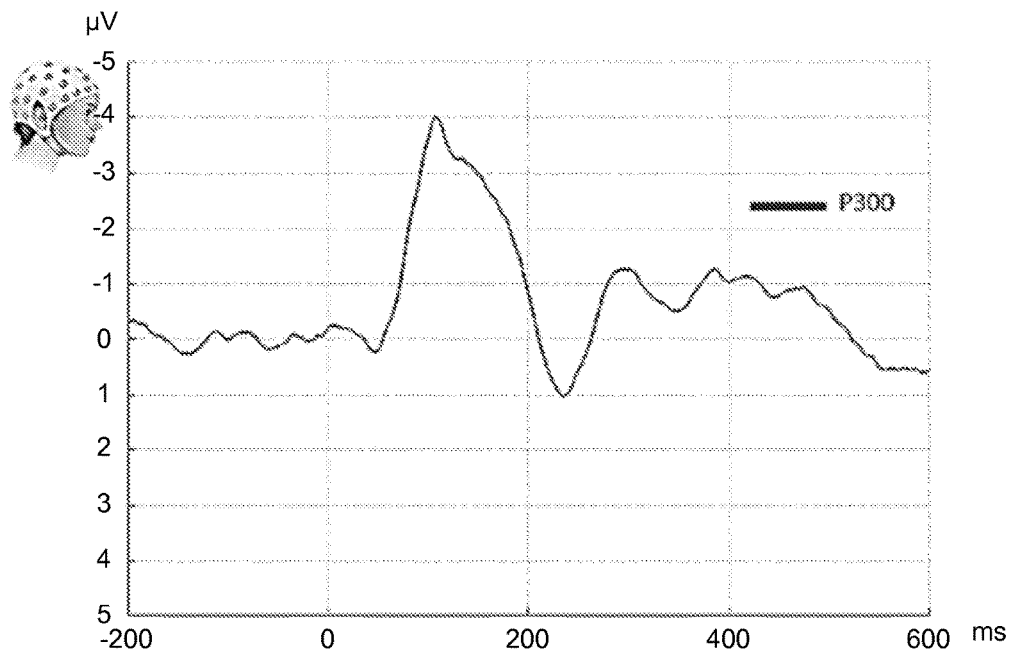

FIGS. 9A and 9B show data plots of exemplary ERP processing and analysis results for human subjects using an existing software tool (FIG. 9A) and the custom-designed program (e.g., using MATLAB script) (FIG. 9B) from an exemplary P300 data set. The data plots depict waveforms from the human subjects using the Cz electrode channel. For example, the data plots of FIGS. 9A and 9B illustrate the pattern of the P300 ERP in healthy human subjects, under no physiological treatment. For example, the P300 is a positive-going waveform that reflects the response to the deviant stimuli. The exemplary P300 ERPs calculated using the existing software tool or the exemplary custom-designed script are consistent, e.g., illustrating the reliability of the exemplary custom-designed program.

The exemplary implementations of the disclosed methods and systems for evaluating vulnerability and progressive pathology associated with neuropsychiatric or neurological disorders, as described above, demonstrated the efficacy and other advantages to detect the MMN and P300 ERPs, e.g., which are associated with disorders such as schizophrenia and Alzheimer's disease Implementations of the disclosed technology can use a modified or different specific stimuli presentation paradigm and EEG acquisition system to "target" different ERPs associated with other neurological and/or neuropsychiatric disorders of interest.

Figure 10:
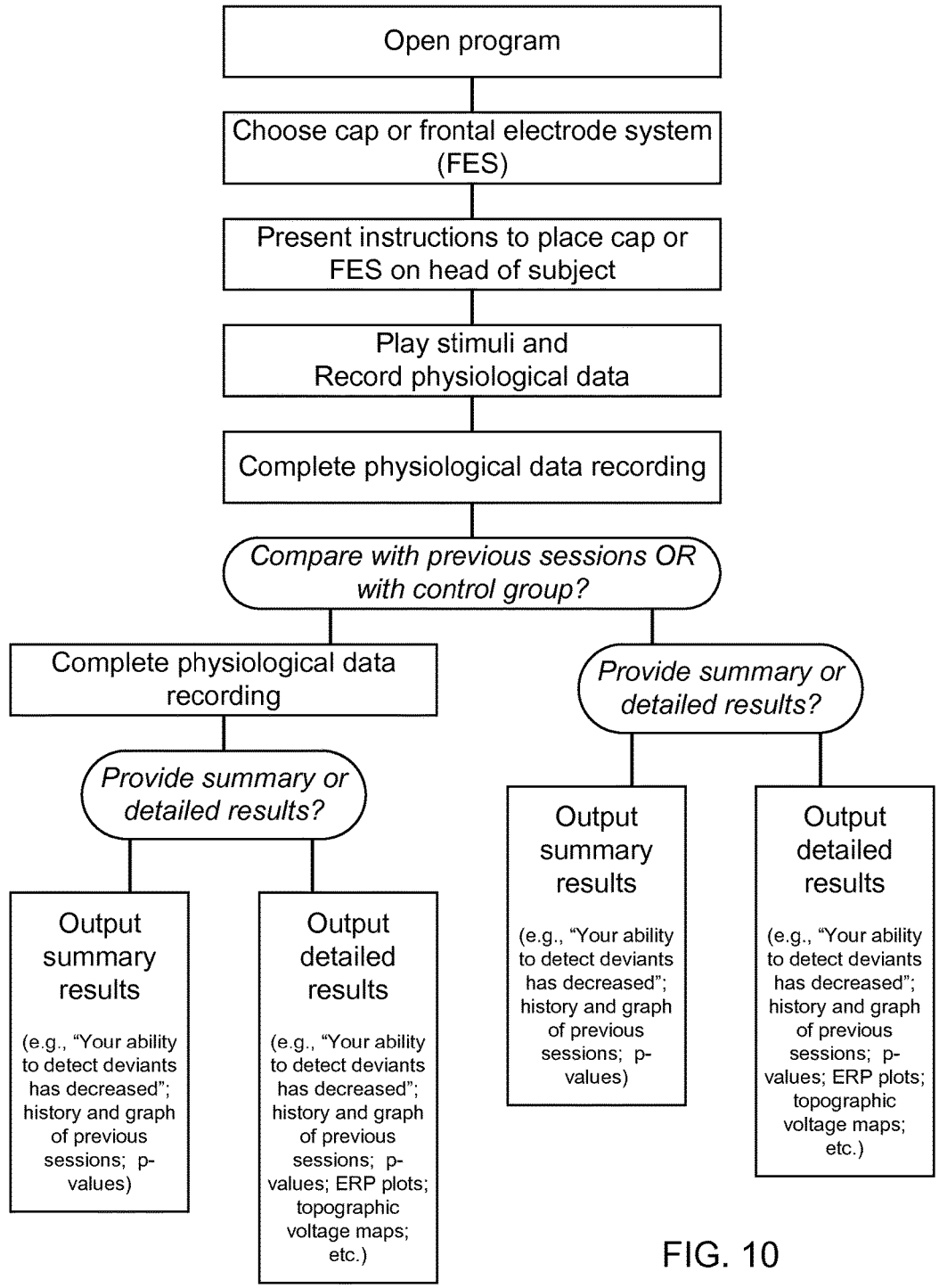
FIG. 10 shows a process diagram of an exemplary user procedure for monitoring vulnerability to or progressive pathology of a neuropsychiatric and/or neurological disorder.

FIG. 10 shows a process diagram of an exemplary procedure for a user to implement, e.g., such as a physician or patient, for monitoring vulnerability to or progressive pathology of a neuropsychiatric and/or neurological disorder. In the diagram of FIG. 10, the nonrectangular text boxes reflect possible queries the program may ask the user (e.g., operator) to tailor the exemplary application toward the desired goal. As shown in the diagram, for example, after opening the program, the operator can receive instructions on how to place the electrode cap or exemplary frontal electrode sensor system onto the head of the subject. Subsequently, for example, the operator can be presented with instructions to begin the stimuli presentation, which also can begin data recording simultaneously with or prior to the presentation of stimuli. The user will be notified of when the data acquisition and stimuli presentation has finished. The next portion of the exemplary procedure can require the user to choose whether he/she wishes to compare the current data acquisition session with previously recorded data acquisition sessions and/or with healthy control group data. For example, by providing this option, a user is able to monitor one's progressive pathology as well as compare the data with a normal population.

The results from the implementation of the exemplary application procedure can be outputted in one of a variety of formats. For example, the results can be outputted into a "Summary" or "Detailed" format, as depicted in the example shown in FIG. 10. In the exemplary Summary results format, users will be provided with a user-friendly or non-expert arrangement of the analyzed results. In some examples of the Summary results format, the application can output a text description, e.g., such as "Your ability to detect deviants (a function of normal sensory memory) has decreased" or ". . . increased" or "remained the same", based on the generated information set produced during the data analysis process. For example, the Summary results format can present quantitative results such as a score that depicts a level of the subject's vulnerability to or progressive pathology of the disorder, as well as statistical results (e.g., p-values) and easy-to-read graph(s) of their previously recorded sessions, which can allow the user to visually monitor the progression of their disorder. In the exemplary Detailed results format, users will be provided with a more sophisticated arrangement of the analyzed results. For example, in addition to exemplary Summary results format, the Detailed results format can also provide ERP graphs and topographic voltage maps (e.g., in the cases in which the user wore a full EEG cap).

II. Exemplary Implementations with MMN and P300 ERPs in Non-Human Primate Subjects (Biological Models) for Assessment of Therapeutic Pharmacological Agents for Neuropsychiatric Disorders II.1. Exemplary Stimuli Presentation Structure In exemplary implementations of the disclosed technology to assess the efficacy of a treatment for a neuropsychiatric disorder, two adult male rhesus macaques (*Macaca mulatta*), e.g., 6 and 7 years old, were used. All procedures and animal care were approved by the Salk Institute Animal Care and Use Committee and carried out in accordance with the US National Institutes of Health Guide for the Care and Use of Laboratory Animals.

The exemplary stimuli presentation structure included a passive auditory intensity oddball paradigm to present different intensity tones to subjects sitting in an isolated, dimly lit room during the implementations. For example, the auditory stimuli included 100 ms (e.g., 10 ms rise/fall) pure sinusoidal tones (e.g., 1500 Hz) of either a low or a high intensity. Frequent (standard) and infrequent (deviant) stimuli were presented 80% and 20% of the time, respectively, as depicted in FIG. 4. The inter-stimulus interval was 700 ms. For example, twelve hundred standard and three hundred deviant stimuli were presented in each recording session. For example, both high-deviant (e.g., low-standard) and low-deviant (e.g., high-standard) conditions were used, e.g., to allow comparison of the responses to identical stimuli (e.g., low or high) in different contexts (e.g., standard or deviant).

The exemplary stimulus presentation paradigm that was used to control the presentation of stimuli in this example was programmed using Cogent 2000. The tones were presented to the exemplary non-human primate (NHP) subjects using an amplifier and speaker. To minimize movement, NHPs were trained to maintain central fixation. For example, the fixation target was a red circle (e.g., 1 degree in diameter) on a black background presented using a 21 inch CRT monitor at 40 cm distance from the NHP subject. The target appeared before the beginning of auditory stimulus presentation and remained visible for the entire duration of the recording session. For example, two methods were used to create the exemplary red, central fixation dot and the blue square stimulus. For the exemplary fixation dot, for example, a computer implemented process (e.g., created using a MATLAB script) was used to create a black background image (e.g., red gun equal to 0; green gun equal to 0; blue gun equal to 0) with a height and width of 350 pixels.

Then, the exemplary script ran a nested for-loop using the standard equation of a circle to alter pixels within a seven pixels length radius to red by changing the image's red gun to 255, the green gun to 0, and the blue gun to 0. For the exemplary blue square stimulus, imaging software was used to create a 157×157 pixel sized image, whose red gun was equal 0, green was equal 0, and blue was equal 255. The exemplary red, central fixation dot was used to help the NHP subjects maintain fixation throughout the recording sessions.

The exemplary computer implemented process was used to configure the display, a Cogent 2000 log file, parallel port, and sound card. Additionally, the exemplary computer implemented process was used to load in the auditory stimuli (e.g., low and high tones) and the visual stimuli (e.g., fixation dot and blue square) into memory buffers. Also in the exemplary implementations using NHP subjects, for example, the exemplary process did not present two or more deviant stimuli consecutively in order to create a greater perception of deviancy. For example, this was achieved by creating presentation order comprised of an array of "1's" and "2's." For example, the "1's" represented standard stimuli, and the "2's" represented deviant stimuli. In these implementations, for example, the aforementioned steps were executed prior to stimulus presentation in order to reduce computational load and increase latency precision.

For example, within the presentation for loop (of the exemplary MATLAB script of the exemplary computer implemented process to produce the fixation target), the fixation dot was presented and remained visible to the NHP subject throughout the entire block. Then, the loop iterated down the presentation order. When it encountered a "1", the exemplary computer implemented process would first send an event marker/trigger to the physiological data acquisition system (e.g., EEG recording computer), followed immediately by the presentation of the standard stimulus (e.g., low tone for condition 1; high tone for condition 2). Likewise, when it encountered a "2", the exemplary computer implemented process would first send an event marker/trigger to the exemplary EEG recording computer, followed immediately by the presentation of the deviant stimulus (e.g., high tone for condition 1; low tone for condition 2). The event marker/trigger indicated which stimulus (e.g., low or high) was presented. For example, each auditory stimulus was followed by an inter-stimulus interval (ISI) of 700 ms.

The NHP subjects were trained to maintain central fixation through positive reinforcement using standard. Precise eye position control was not a requirement in these exemplary implementations. For example, the fixation target was merely an aid to help minimize ocular movement, and as such, fixation was not quantified.

II.2. Exemplary EEG Data Collection/Recordings

For example, EEG scalp recordings were acquired with the Vision Recorder software using a BrainAmpMR system. An exemplary custom-designed 22-channel NHP EEG cap with AgCl electrodes was developed and used for the non-human primate subject data collection (e.g., PCB Ribbon Cable for BrainCap-MR with 5 k resistors; BrainCap MR Box 1.2; sintered ring electrodes with 1.5 mm touchproof safety socket termination and 120 cm heavy-duty leadwire).

Figure 11:
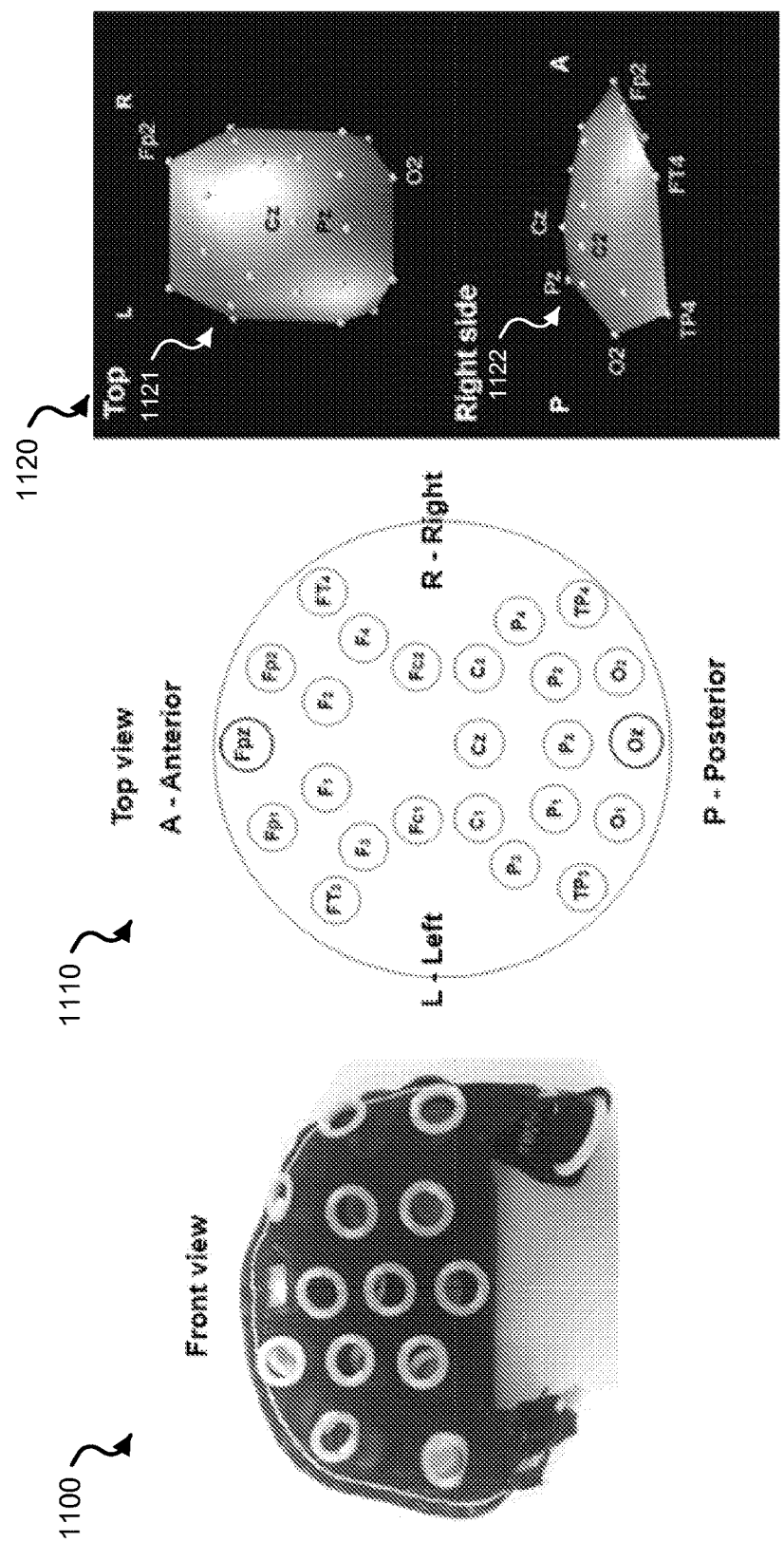
FIG. 11 shows an exemplary 22-channel non-human primate EEG cap of the disclosed technology.

FIG. 11 shows an image and diagrams illustrating the exemplary custom-designed 22-channel NHP EEG cap. In FIG. 11, an image 1100 is shown of the exemplary NHP EEG cap showing the frontal view of the exemplary arrangement of EEG electrodes for the detection cap. A diagram 1120 is shown depicting a tridimensional reconstruction of the top side (diagram 1121) and right side (diagram 1122) schematical views of the exemplary 22 electrodes' location in the exemplary NHP EEG cap. FIG. 11 also shows a diagram 1110 depicting a two dimensional view of the 22 electrodes' position in the exemplary NHP EEG cap. The exemplary NHP EEG cap includes a stretchable material configured in a two-panel design that allows for a snug fit over the monkey scalp. For example, the exemplary stretchable material can include a medium weight, powernet fabric material. The NHP EEG cap has 22 channels that provides an electrode density identical to the human 64-channel cap. The exemplary NHP EEG cap was designed to fit the same set of AgCl electrodes from the BrainAmpMR system used in human subjects. For example, the exemplary NHP EEG caps can be used to provide an intrinsic component of the exemplary systems of the disclosed technology for assessment of potential therapeutic pharmacological agents for neuropsychiatric and/or neurological disorders, e.g., using non-human primates. The exemplary NHP EEG cap can provide 'full-scalp coverage' for the non-human primate subjects, and provides advantages, for example, including enabling both broad and integrative data collection, as well as direct comparison with brain signals acquired in human subjects. Fabrication of the exemplary NHP EEG cap included cutting two half-moon shaped pieces, which were subsequently stitched together. Afterward, small, plastic belt loops or other securement components were attached onto each end to form the chin strap. Lastly, 22 electrode holders were placed onto the cap at particular locations on the stretchable material corresponding to the 22 electrodes shown in the diagrams 1110 and 1120 of FIG. 11.

The exemplary EEG data collection technique for the NHP subjects included the following preparation steps. For example, (1) the NHP head position was stabilized, e.g., rigid head fixation was required, so a MR-compatible headpost was designed for surgical implantation on the dorsal cranium. For example, (2) the NHP EEG cap was placed. In the exemplary implementations, the exemplary customized NHP EEG cap shown in FIG. 11 was used for macaque subjects. For example, (3) an EEG restraining chair was used for the exemplary NHP subjects. For example, a custom-built MR-compatible chair was designed using MR-compatible materials. The NHPs were restrained inside the chair in a sphinx-like position with head protruding, stabilized, and faced forward. For example, (4) a 3D scalp reconstruction with electrode positions was created. For example, using an exemplary Polhemus Fastrak system, a 3D reconstruction of each animal's scalp was created with the exact position of each electrode pinpointed. This allowed the creation of topographic maps of voltage distribution for the acquired EEG datasets.

The NHP subjects were trained to visually fixate prior to physiological signal recording. For example, an exemplary computer implemented process was developed to train the NHP subjects on visual fixation (e.g., two scripts programmed on CORTEX.

Implementation of the first exemplary script included displaying an exemplary red, central fixation dot on a black background measuring one visual degree in diameter. When the NHP subject looked at the fixation dot within a 4°×4° visual degree window for a minimum of 1000 ms, the subject would receive a small juice reward (e.g., from a Crist Instrument reward system), followed by an inter-stimulus interval (ISI) of 0 ms. For example, an ISCAN eye-tracking system (ETL-200) to monitor eye movements was used. This exemplary procedure was used to train subjects to fixate and rapidly associate the fixation dot with reward. Implementation of the second script also included a red, central fixation dot measuring one visual degree in diameter. However, for example, in parallel, a high contrast, black and white, abstract image would appear behind the fixation dot for 750 ms, followed by a jittered ISI of 750 ms to 1000 ms. For example, the script controlled the flashing of a series of four to six abstract images and required subjects to fixate during each image presentation. If the NHP subject maintained fixation within a 4°×4° visual degree window centered on the fixation dot for each image presentation, the subject would receive a small juice reward, while simultaneously presented with a visual blue square stimulus which indicated reward and a pause between trials. Each blue square stimulus was presented for 1500 ms and was immediately followed by the next series of abstract images.

The training and recording processes included, firstly, securing the NHP subject into the exemplary custom-built, MRI compatible chair. This provided both the restraint and comfort for the animal subject. For example, for the recording process, the chair was laid down horizontally onto a table in the recording chamber. This allowed the NHP subject to face the presentation monitor and speaker in a sphinx position. Then, the EEG cap was placed onto the NHP subject's head and secured the head to the restraint chair. Next, Signa electrode gel was injected using a curved, plastic syringe under each of the cap's electrodes to create a conductive bridge between the electrode itself and the subject's scalp. We also used wooden Q-tips to massage the gel in order to build a stronger conductance by lowering the impedance. Afterward, the recording chamber's doors were closed and the lights were completely turned off. Throughout both the training and recording processes, NHP subjects were closely monitored using an infrared camera.

II.3. Exemplary EEG Data Analysis

The exemplary EEG data was analyzed using Analyzer 2.0 software. The exemplary EEG data analysis procedure included first re-referencing the data sets from the original recording references to identical posterior occipital channels, as a new comparable reference between species (e.g., human: Oz, O1, O2, PO7, PO8, P7, P8; rhesus macaque: Oz, O1, O2, P3, P4). This was followed by band-pass filtering (e.g., Low Cutoff: 0.1 Hz, High Cutoff: 50 Hz) and changing the sampling rate from 1000 Hz to 250 Hz based on spline interpolation. For example, in order to avoid analysis artifacts stemming from differences in sample size, the exemplary data sets were first segmented relative to the deviant markers position (e.g., start: −1000 ms, end: 600 ms), so that it would include all deviant trials (e.g., N=300) and only the standard trials (e.g., N=300) immediately preceding the deviants. Subsequently, for example, the resulting epochs were segmented relative to either the deviant or the standard marker positions (e.g., start: −200 ms, end: 600 ms) identifying the relevant deviant and standard epochs. For both standard and deviant epochs, a baseline correction (e.g., start: −200 ms, end: 0 ms) was applied, a multiple features artifact rejection tool was applied (e.g., applied to all channels; maximal allowed voltage step: 50 µV/ms; maximal allowed difference of values in intervals: 200 µV; lowest allowed activity in intervals: 0.5 µV). The ERP (average) was then calculated for each channel and condition (e.g., high-standard, low-standard, high-deviant and low-deviant). For example, difference waves (e.g., deviant minus standard) were calculated for both conditions (e.g., low-deviant minus low-standard and high-deviant minus high-standard), and subsequently the low and high difference waves were averaged to yield the MMN component, and the low and high responses to deviants were averaged to yield the P3 component.

II.4. Identification of Non-Human Primate ERPs

In the exemplary implementations, the exemplary MMN and P3 ERP components were identified first in humans, and then the homologous components in non-human primates were identified. For example, both ERP components were identified using established criteria that employed the same testing paradigm (oddball paradigm where the MMN is the difference wave of deviant minus standard stimuli and the P3 is observed on deviant stimulus trials), and the timing, electrode location, voltage scalp distribution, and neural generators were ascertained for these exemplary ERP components. For example, after identifying the MMN, a 40 ms window was established around the peak amplitude in the average ERP wave. This exemplary time-window was used to extract peak amplitude values per NHP subject from single trials. For example, these values were then used for statistical analysis in a 2-way repeated measures ANOVA (e.g., factor 1: standard vs. deviant; factor 2: high vs. low) for each species. The P3 component was investigated in the averaged response to low and high deviants. Similarly, for example, after identifying the P3 components in humans and monkeys, a 40 milliseconds window was established around the peak amplitude in the ERP wave, and that window was used to extract the mean amplitude values from single trials. For example, the statistical significance for a P3 response in each species was calculated using a t-test.

II.5. Exemplary EEG Data Analysis Using Custom-Designed Program

For example, similar to the exemplary implementations with human subjects to assess vulnerability or progressive pathology to a neurological or neuropsychiatric disorder, the MMN and P300 components were calculated using an existing software package (e.g., BrainVision Analyzer 2.0) and the exemplary custom-designed computer implemented analysis process (e.g., programmed in MATLAB script) to process the MMN and P300 data from the NHP subjects to create the ERP waveforms. The exemplary program was implemented to automatically process the data (e.g., performing signal processing steps such as filtering, channel removal, re-sampling, etc.), calculate the MMN difference wave ERP, calculate the P300 ERP, and perform statistical analyses on the given data.

II.6. Characterization of MMN ERP in Humans in Non-Human Primates

For example, using established characterizations of the timing and scalp topography of the MMN component in humans, as well as proposed NHP MMN definitions resulting from epidural recordings, MMN ERPs were found in both species. In macaques, for example, the MMN duration was from approximately 48 ms to 120 ms, with a peak amplitude of −1.62 µV at 88 ms (F(1,409)=11.17, p=0.000), and a central scalp distribution.

Figure 12A:
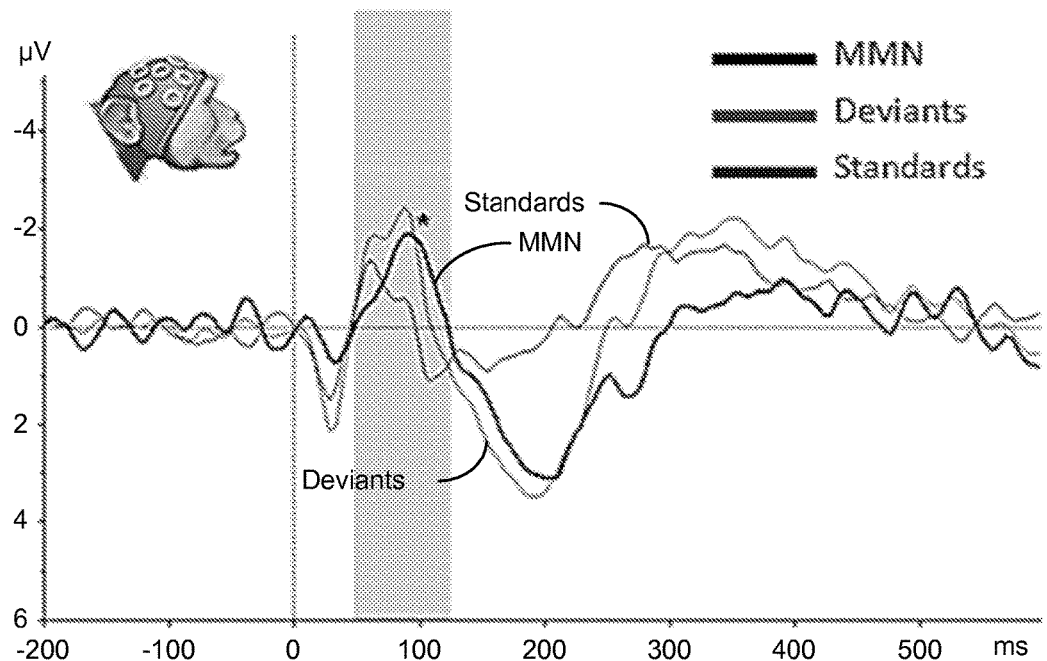
FIGS. 12A and 12B show data plots of exemplary ERP processing and analysis results using an exemplary dataset of the mismatch negativity ERP for non-human primate subjects under no physiological treatments.
Figure 12B:
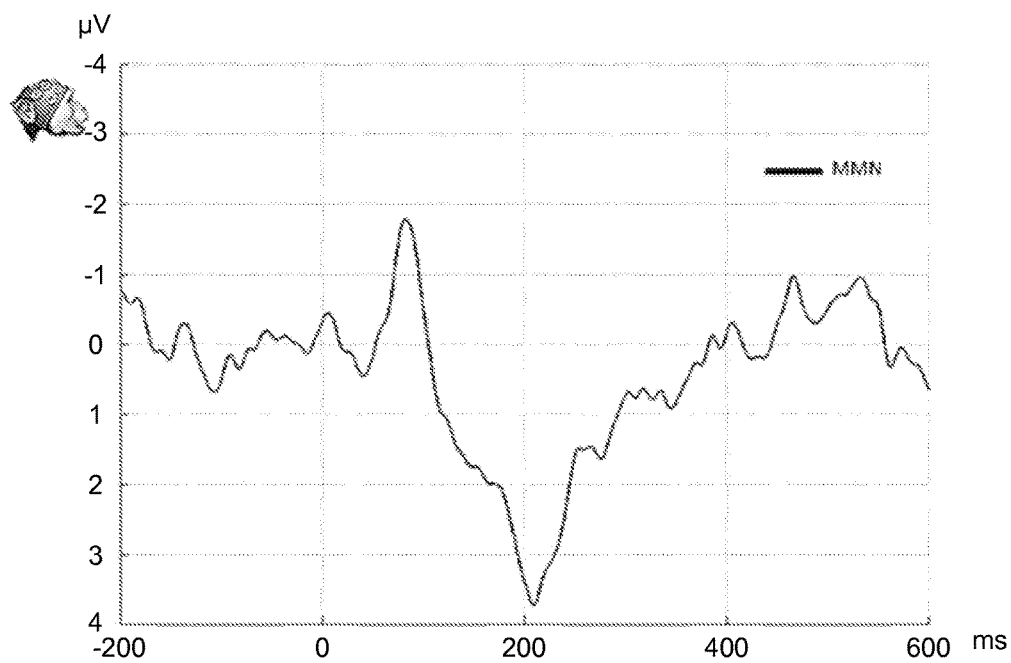

FIGS. 12A and 12B show data plots of exemplary ERP processing and analysis results for NHP subjects using an existing software tool (FIG. 12A) and the custom-designed program (e.g., using MATLAB script) (FIG. 12B) from an exemplary MMN data set. The data plots depict waveforms from the non-human primate subjects using the Cz electrode channel. For example, the data plots of FIGS. 12A and 12B illustrate the basic pattern of the MMN in non-human primate subjects under no physiological treatments. Similar to the MMN response in human subjects, the data plot in FIG. 12A includes the waveforms for the standards and deviants and shows the strong discrimination between standards and deviants, as evidenced by the MMN, reflecting the difference of the deviant waveform minus the standard waveform. Likewise, in FIG. 12B, the exemplary ERP processing and data analysis using the exemplary custom-designed program yielded substantially the same results for the MMN waveform in the expected time interval.

II.7. Characterization of the P300 ERP in Humans and Non-Human Primates

As with the MMN, the P300 was defined using established characterizations and was investigated in the averaged response to low and high deviants. As with the MMN, the P3 component showed consistency across species. For example, in the macaques, the duration was from approximately 104 ms to 248 ms, with peak amplitude of 3.5 µV at 196 ms (t=10.36, p=0.000). Both species presented a central-parietal scalp distribution.

Figure 13A:
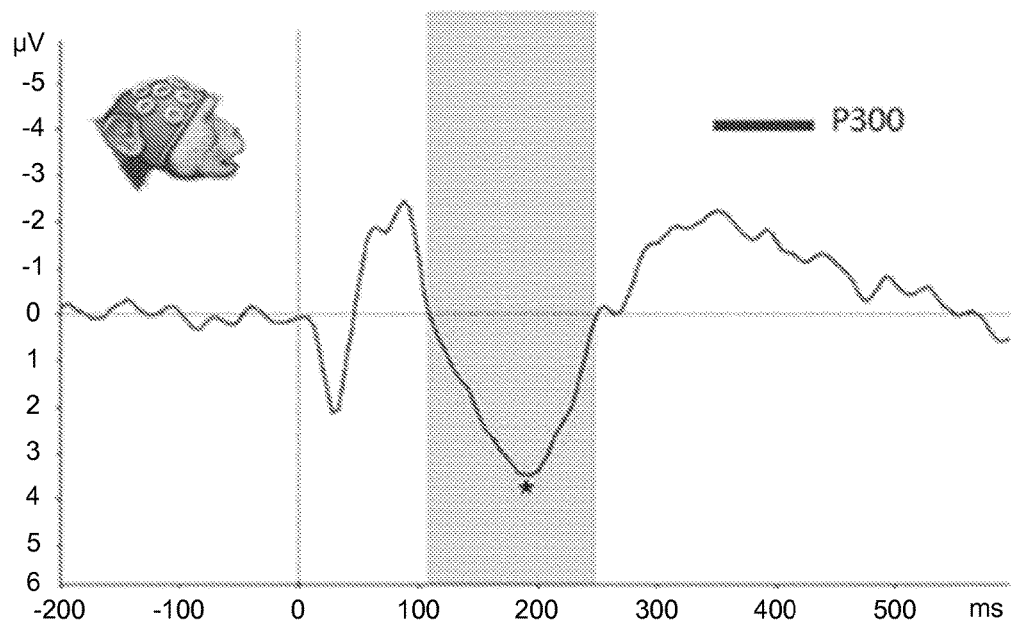
FIGS. 13A and 13B show data plots of exemplary ERP processing and analysis results using an exemplary dataset of the P300 ERP for non-human primate subjects under no physiological treatments.
Figure 13B:
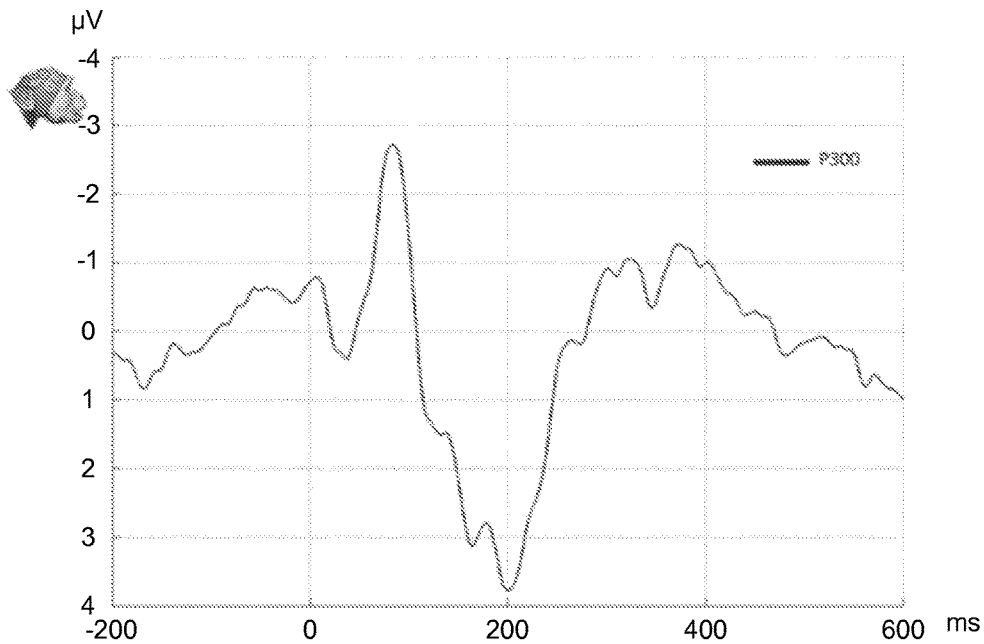

FIGS. 13A and 13B show data plots of exemplary ERP processing and analysis results for NHP subjects under no physiological treatments using an existing software tool (FIG. 13A) and the custom-designed program (e.g., using MATLAB script) (FIG. 13B) from an exemplary P300 data set. The data plots depict waveforms from the non-human primate subjects using the Cz electrode channel. For example, similar to the P300 response in human subjects, for example, the P300 in non-human primate subjects is a significant positive-going voltage potential, reflecting the response to the deviant stimuli. The exemplary P300 ERPs calculated using the existing software tool or the exemplary custom-designed script are consistent in the expected time interval, e.g., illustrating the reliability of the exemplary custom-designed program.

The aforementioned exemplary implementations showed the identification the relevant ERPs in the exemplary macaque model (e.g., MMN and P300), and its comparison with the same ERPs in humans. Further implementations of the disclosed systems and methods assess the response of a subject to manipulations of physiological conditions using a "symptom inducing agent" or a potential "recovery inducing agent" (e.g., potential therapeutic drug) in order to produce temporary deficits and test potential recovery using this exemplary NHP animal model.

II.8 Exemplary Implementations for Testing a Symptom Inducing Agent (Ketamine) and Saline Vehicle with MMN and P300 ERPs in NHP Subjects Under Different Physiological Conditions Exemplary implementations of the disclosed systems and methods were performed for evaluating the effects of ketamine using the MMN and P300 ERPs in the exemplary macaque model under three physiological conditions, e.g., (i) acute subanesthetic ketamine infusion (e.g., 1 mg/Kg), (ii) saline (vehicle) infusion, and, (iii) 5 hours after acute subanesthetic ketamine infusion.

As shown in FIGS. 14A-15B, ketamine infusion led to a significant reduction of both the MMN (ketamine vs. saline (F(1,290)=4.47, p=0.035)) and the P300 (ketamine vs. saline (F(1,301)=27.73, p=0.000) amplitudes when compared to the vehicle "saline". The effects of ketamine were no longer significant 5 h after infusion (MMN ketamine vs. 5 h-post ketamine (F(1,403)=7.97, p=0.005; 5 h-post ketamine vs. saline (F(1,290)=0.20, p=0.652; P3 ketamine vs. 5 h-post ketamine (F(1,411)=44.34, p=0.000); 5 h-post ketamine vs. saline (F(1,301)=0.06, p=0.803;)). No significant latency differences were observed. Taken together, these exemplary results demonstrate that the NMDA receptor antagonist ketamine can significantly reduce the amplitude of the MMN and P3 ERP components in the macaque.

Figure 14A:
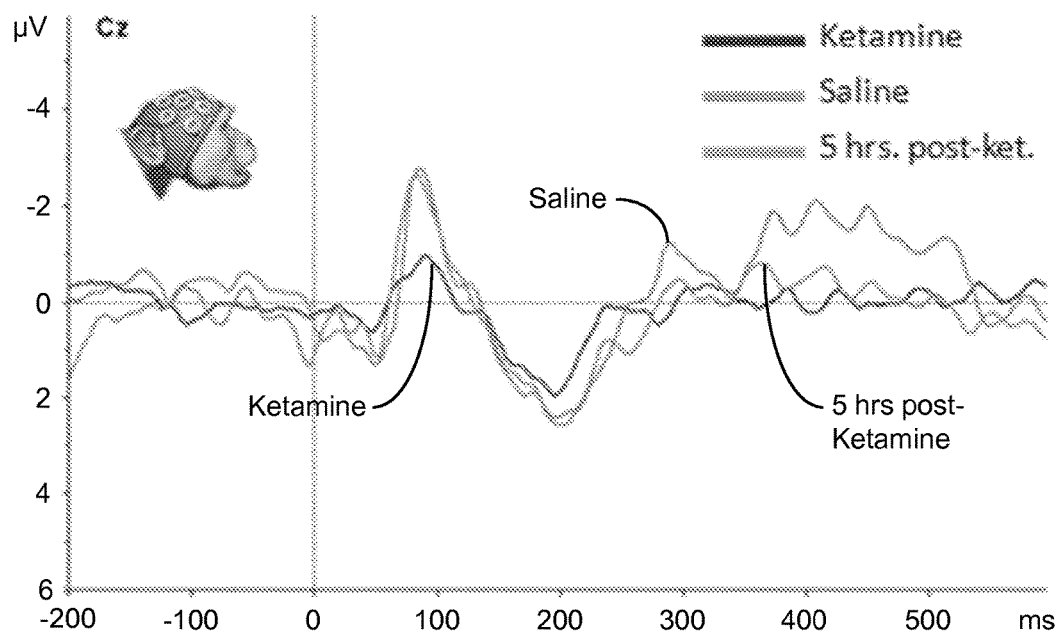
FIGS. 14A and 14B show data plots of exemplary ERP processing and analysis results using an exemplary dataset of the mismatch negativity ERP for non-human primate subjects across different physiological treatments.
Figure 14B:
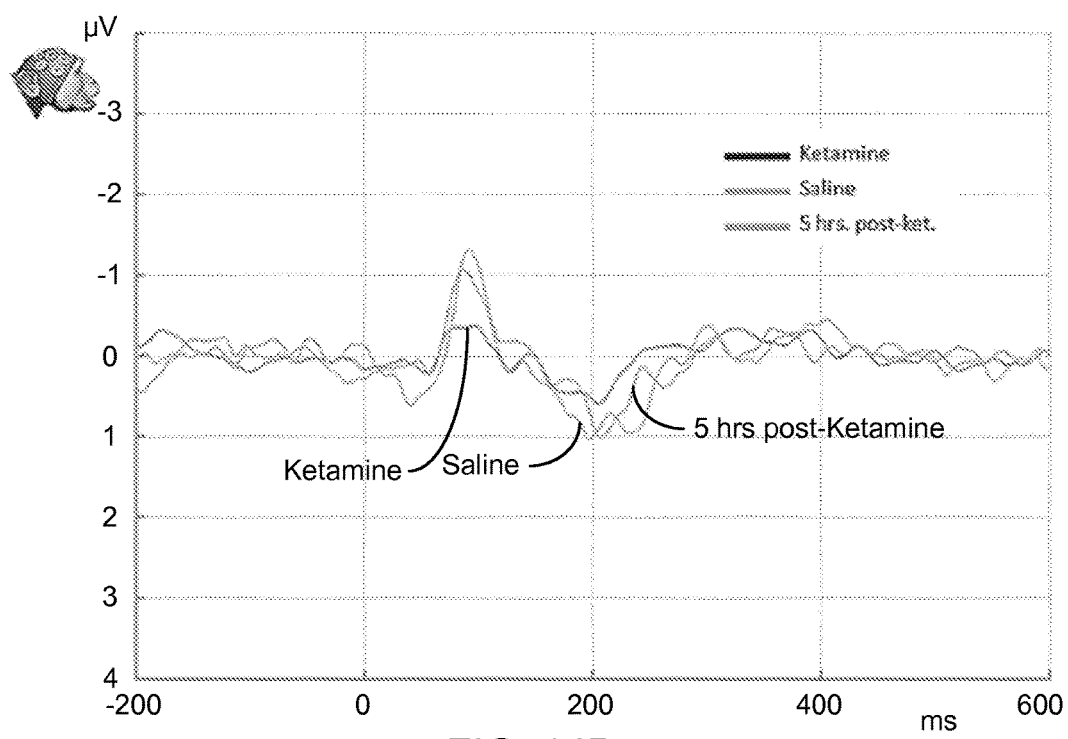

FIGS. 14A and 14B show data plots of exemplary ERP processing and analysis results from an exemplary MMN data set for NHP subjects across the different physiological conditions using an existing software tool (FIG. 14A) and the custom-designed program (e.g., using MATLAB script) (FIG. 14B). The data plots depict waveforms from the non-human primate subjects using the Cz electrode channel. For example, the waveforms in FIGS. 14A and 14B reflect the MMN response in non-human primate subjects under different physiological treatments, e.g., including ketamine, saline/control, and 5 hours post-ketamine. The data plot in FIG. 14A shows reduction in the MMN amplitude under the ketamine treatment, e.g., when compared with the saline/control injection. This reduction reflects an attenuation of the response to the deviant stimuli. More specifically, for example, a reduction of the MMN strongly suggests that the subjects are having difficulty detecting the deviant stimuli. Functionally, this suggests a temporary dysfunction in sensory memory processing, a symptom often common in patients with schizophrenia and other neuropsychiatric disorders. Moreover, for example, these symptoms are shown to have disappeared, and the animal model (e.g., non-human primates) shows full recovery as early as at least 5 hours post injection. Likewise, in FIG. 14B, the exemplary ERP processing and data analysis using the exemplary custom-designed program, allowing for fast automation and "ease of use," yielded substantially the same results.

Figure 15A:
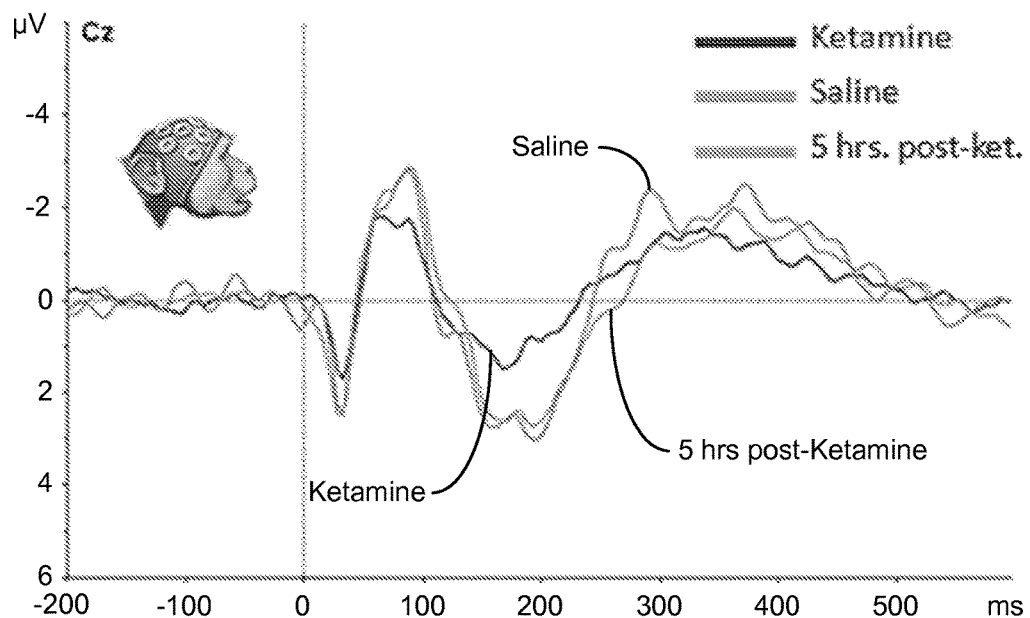
FIGS. 15A and 15B show data plots of exemplary ERP processing and analysis results using an exemplary dataset of the P300 ERP for non-human primate subjects across different physiological treatments.
Figure 15B:
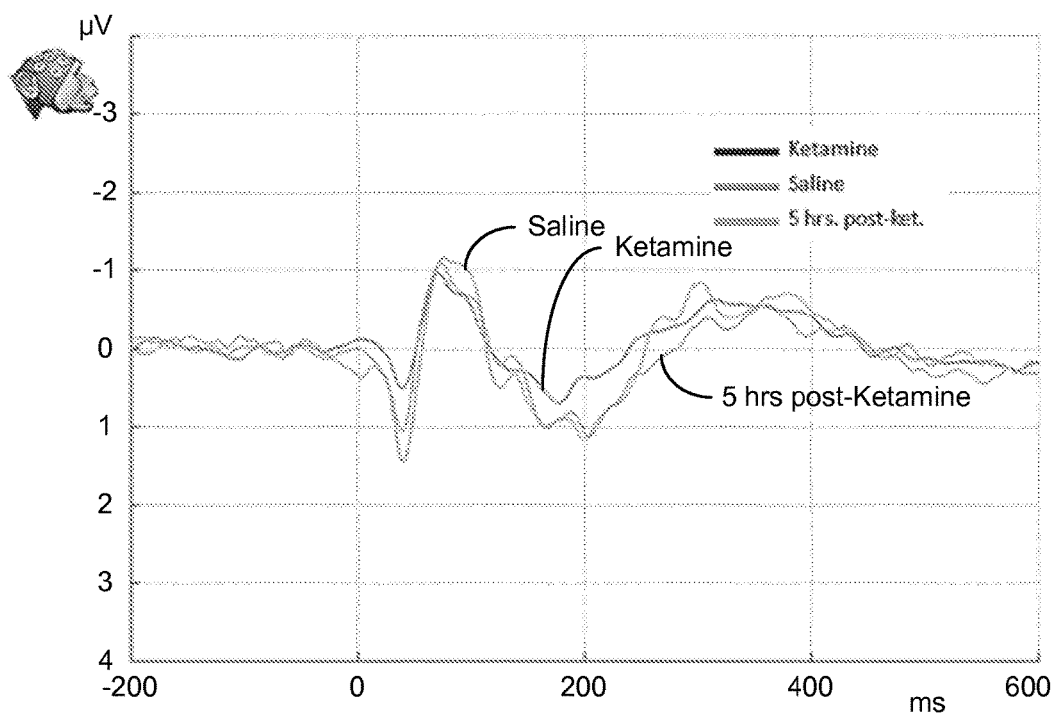

FIGS. 15A and 15B show data plots of exemplary ERP processing and analysis results from an exemplary P300 data set for NHP subjects across the different physiological conditions using an existing software tool (FIG. 15A) and the custom-designed program (e.g., using MATLAB script) (FIG. 15B). The data plots depict waveforms from the non-human primate subjects using the Cz electrode channel. For example, the waveforms in FIGS. 15A and 15B reflect the P300 response in non-human primate subjects under different physiological treatments, e.g., including ketamine, saline/control, and 5 hours post-ketamine. As shown by both the existing software and the exemplary program in FIGS. 15A and 15B, respectively, there is a reduction in the P300 amplitude under the ketamine treatment, e.g., when compared with the saline/control injection, which reflects an attenuation of the response to the deviant stimuli. As in the examples using the MMN ERP, functionally, this suggests a dysfunction in the subjects' ability to redirect their attention to the deviant stimuli, e.g., which can be affiliated with schizophrenia and other neuropsychiatric or neurological disorders. As depicted by the waveforms in the data plots of FIGS. 15A and 15B, these symptoms have disappeared, and the animal model (non-human primates) shows full recovery as early as at least 5 hours post injection.

The exemplary implementations of the disclosed methods and systems for assessing potential therapeutic pharmacological agents for neurological or neuropsychiatric disorders using a non-human primate biological model, as described above, demonstrated the efficacy and other advantages to detect physiological responses (e.g., the MMN and P300 ERPs) associated with such disorders as well as test different substances—to induce a "desired" physiological conditions in an animal model—and its modulations of these neural markers.

Figure 16:
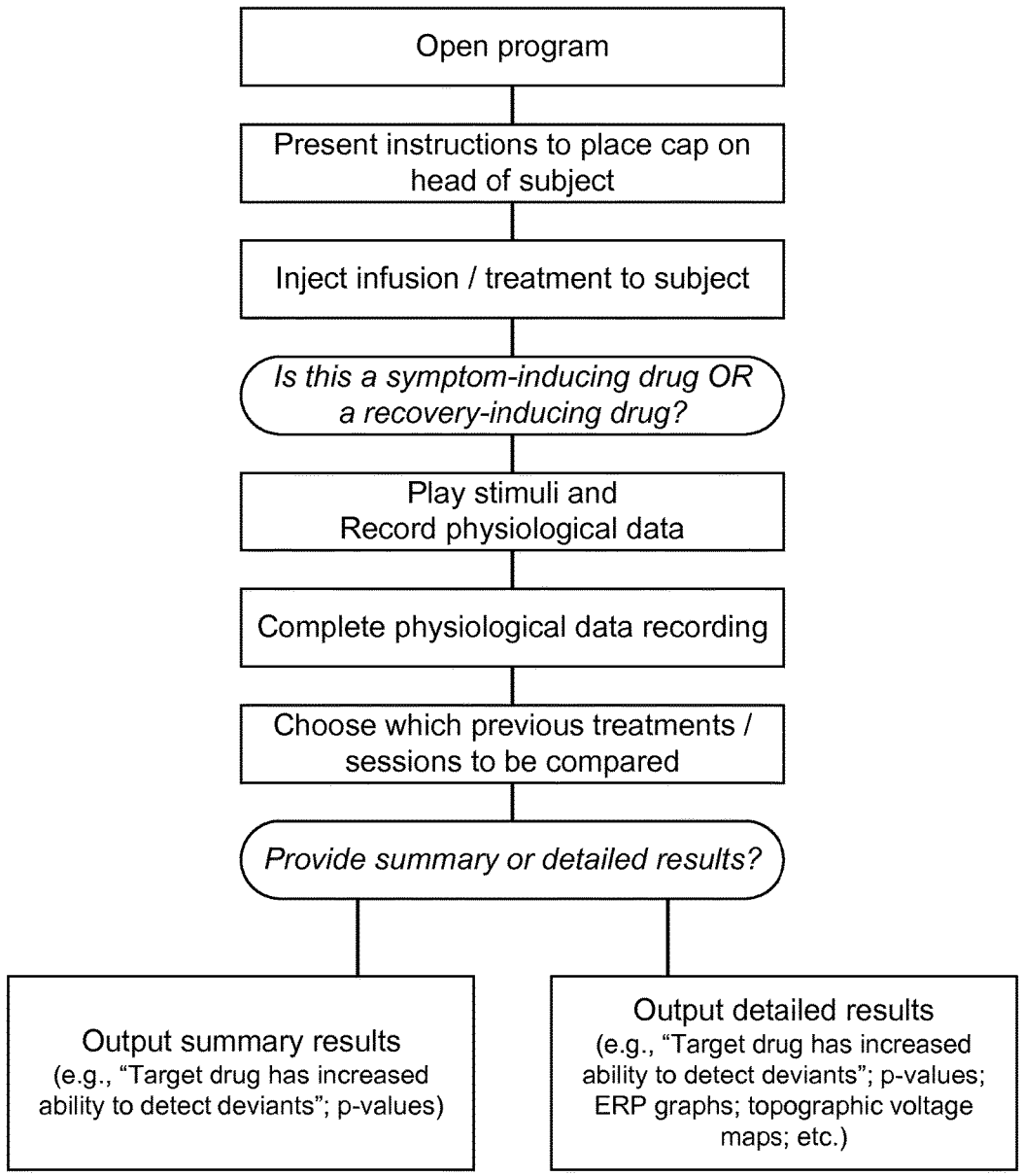
FIG. 16 shows a process diagram of an exemplary user procedure for assessing the efficacy of therapeutic pharmacological agents for a neurological or neuropsychiatric disorder.

FIG. 16 shows a process diagram of an exemplary procedure for a user to implement, e.g., such as a pharmaceutical drug researcher using non-human primates as an animal model, for assessing the efficacy of potential therapeutic pharmacological agents for neurological or neuropsychiatric disorders. In the diagram of FIG. 16, the nonrectangular text boxes reflect possible queries the program may ask the user (e.g., operator) to tailor the exemplary application toward the desired goal. As shown in the diagram, for example, after opening the program, the operator can receive instructions on how to place the cap on the subject's (e.g., non-human primate's) head. The user will be instructed to inject their drug of interest and specify whether it is a "Symptom-inducing" or a "Recovery-inducing" agent. An example of a symptom-inducing drug can include a sub-anesthetic dose of ketamine, which is an NMDA receptor antagonist. A recovery-inducing drug can be any target drug a researcher, for example, would be testing to alleviate or cure a neuropsychiatric disorder. One possible scenario would be the simultaneous use of both a symptom-inducing drug and a recovery-inducing drug. For example, a researcher could cause temporary sensory and/or cognitive deficits (e.g., the decrease of the MMN and P300 amplitudes) followed by inducing recovery via a target drug. By doing so, the user would be able to test the efficacy of the target drug against the effects of an NMDA receptor antagonist such as ketamine, simulating the disease.

After injection(s), for example, the operator can be presented with instructions to begin the stimuli presentation (e.g., including selecting the profile category), which also can begin data recording simultaneously with or prior to the presentation of stimuli. The user will be notified of when the data acquisition and stimuli presentation has finished. The next portion of the exemplary procedure can require the user to specify whether he/she wishes to compare the current data acquisition session with previously recorded data acquisition sessions (e.g., previously recorded treatments) and/or with healthy control group data.

The results from the implementation of the exemplary application procedure can be outputted in one of a variety of formats. For example, the results can be outputted into a "Summary" or "Detailed" format, as depicted in the example shown in FIG. 16. In the exemplary Summary results format, users will be provided with a non-expert user-friendly arrangement of the analyzed results. In some examples of the Summary results format, the application can output a text description, e.g., such as "Target drug has increased ability to detect deviants,", based on the generated information set produced during the data analysis process. For example, the Summary results format can present quantitative results such as a score that depicts a level of pathology of the neurological or neuropsychiatric disorder. Moreover, for example, Summary results format can present to users statistical p-values of the comparison of standards and deviants. In the exemplary Detailed results format, users will be provided with a more sophisticated arrangement of the analyzed results. For example, in addition to exemplary Summary results format, the Detailed results format can also provide ERP graphs and topographic voltage maps.

Guided Classification Techniques

In some aspects, for example, the disclosed technology includes systems and methods for data and signal processing including implementing classifiers, test statistics, and machine learning algorithms to the analysis of the acquired physiological data. By nature, for example, EEG data is typically noisy due to electrical interference, muscle activity, direct current (DC) offset, sweat, and other factors. This poor signal-to-noise ratio (SNR) leads to the need to typically collect data over a vast number of trials, in order to acquire a large enough sample size that allows accurate detection of the investigated effects. The disclosed technology includes classification algorithms and customized test statistics that can be applied for EEG or other physiological signal data analysis in order to significantly decrease the necessary number of trials, e.g., thereby reducing testing time.

The exemplary classifier methodologies described herein use identifiable cognitive and physiological parameters to structure the relevant features in a classification methodology to infer brain states, and correlated potential pathologies, from neural signals. These features pertain to, for example, specific electrodes and specific time windows of interest, e.g., where a known ERP shows fluctuations that relate to the controlled stimulus and whose statistics can co-vary with disease state, vulnerability to disease, and/or presence of pharmacological agent. For example, after providing stimuli and collecting statistical information, a profile can be produced that provides a value of the degree of the effect of the exemplary treatment to the neurological or neuropsychiatric disorder (e.g., such as a pharmacological agent), the severity of the disorder, or the extent to which the subject is vulnerable to the disorder.

Within the context of classifying whether one hypothesis as compared to another, an example pre-processing stage of an exemplary guided classification technique is as follows. Identify a relevant electrode of the physiological data acquisition module (e.g., EEG scalp electrode) pertaining to the type or class of stimuli. For example, the identifying can include denote the EEG signal data in a specific trial k under condition c in time bin t as $y[c,k,t]$. For example, a condition could include saline vs. ketamine, or a healthy vs. a vulnerable subject within the context of a particular neurological or neuropsychiatric disorder (e.g., schizophrenia). Average ($y[c,k,t]$: k=1, . . . , K) over k to create $y[c,t]$. One core hypothesis to test is, for example: H0 (null): the statistics of $y[1,t]$ and of $y[2,t]$ are the same; H1 (alternate): the statistics of $y[1,t]$ and of $y[2,t]$ are not the same.

For example, using a supervised methodology, the data can be first split into known categories based upon a "training" paradigm, e.g., where the extent to which the pharmacological agent has affected the brain state is clear. For example, a saline injection is one extreme, whereas a high dose of a pharmacological agent is another. With this, data sets can be tested to understand the effect of the pharmacological agent, e.g., by using a regression to characterize a continuous value of the degree to which the pharmacological agent is affecting the brain state of interest. For example, the time window of interest of the event-related potential can be pre-specified based upon the known cognitive neuroscience and neurology related to the specific brain marker of interest.

For example, in an unsupervised setting, no training data is used. Instead, for example, we treat this as a composite hypothesis testing problem in which there is a range of possible parameters. For such paradigms, for example, a natural assumption (after a Normality test has ensued) is that $y[1,t]-y[2,t]$ is Normal. Thus, under the null hypothesis, this difference has 0 mean and unknown variance. Under the alternate hypothesis, the difference has a non-zero mean and unknown variance (not necessarily the same variance as under H0).

Because the variance under H0 and the mean variance under H1 are unknown, this is a composite hypothesis testing problem: there are many distributions under each hypothesis. A group of unsupervised classifiers pertaining to composite hypothesis testing can be implemented that are theoretically sound in different manners, with different assumptions. For example, a test statistic can be developed, which is a function of the observed data. From this test statistic, a p-value can be calculated or estimated, which is compared to a threshold, e.g., 0.05. If it exceeds 0.05, the null hypothesis is accepted; otherwise, it is rejected.

Test statistics can include methods from, for example, normalized maximum likelihood; and/or standard statistical methods, e.g., such as an F-score for an ANOVA, based upon estimated means and variances After calculating the test statistic, the likelihood of observing a test statistic that is at least as extreme as what was observed is calculated, under the null hypothesis. Because the null hypothesis has an unknown variance, this is a composite hypothesis testing problem and there is not one specific natural way to calculate a p-value. For example, multiple ways can be developed to estimate a p-value. One example includes performing a parametric procedure to evaluate the probability expression using an estimate of P0, assuming a Normal distribution with variance estimated from data. If the distribution of the test statistic, g(d) under H0 is known in closed form (e.g., For t, Z, F, ANOVA tests), then direct calculation can be performed or a lookup table can be used.

If, for example, a more sophisticated test statistic is used (e.g., such as the normalized likelihood ratio), then a Monte Carlo procedure can be implemented to estimate the probability. A non-parametric bootstrap procedure, for example, can estimate a p-value for the normalized maximum likelihood scenario. The aforementioned classifiers mentioned above provide statistical information (e.g., a p-value in the unsupervised case). This can be directly translated to a "degree" of severity by taking a function that monotonically varies with the degree of confidence in the classification. For example, a natural procedure is the "log loss" which assigns a degree of confidence based upon the negative logarithm of a probability.

Exemplary Methodological Solution for Automatic Stimulus Presentation, Data Acquisition, and Data Processing In some implementations of the disclosed systems and methods, a network of computers and analysis techniques are used to elicit, record, and process/analyze the MMN and P300 ERP components, for example. To increase the usability and speed of this system, an exemplary "all inclusive" application system of the disclosed technology can be implemented for automatic stimulus presentation, data acquisition, and data processing. By combining these features into one coherent system, the time, space, and usability needed for effective and accurate data processing are optimized. In one example, the exemplary "all inclusive" application can be implemented on a computer system and be configured using Qt, a "cross-platform application and UI framework" (Qt Developer Network), relying on the exemplary parallel stimulus presentation, data acquisition, and signal processing model of the disclosed technology. The exemplary "all inclusive" application system can also be implemented using other programming languages, e.g., such as Java, in order to build this program both on conventional computer systems (e.g., laptop and server machines, etc.) and on mobile devices (e.g., smartphones and tablet computers, etc.).

In the Qt example, the development was structured to be broadly based. Specifically, for example, the exemplary Qt-based "all inclusive" program can present a variety of stimulus paradigms (e.g., including both visual and auditory), acquire data from various EEG recording hardware, and implement different analysis techniques and steps. On a large scale, for example, the system begins by opening a data thread to acquire EEG data online from a specified source. In this particular example, multiple application programming interfaces (APIs) were used, e.g., allowing the application to acquire data from a variety of devices, e.g., including Brain Products EEG system, a Neurosky Mindset device, an AD8224 amplifier, a TGAM1 amplifier, and an epidermal electronics system, for example. At the same time, a selected stimulus paradigm, such as an auditory oddball sequence, can be initiated and presented to the subject. The stimulus presentation and data acquisition can be run in parallel using multiple computer processors within the same machine. They also can communicate information to each other, such as at what point in time a stimulus was presented. By communicating this type of information, the subsequent signal processing can have specific information as to "where" and "when" relevant and event-related data occurred. Within Qt, s signal processing module was configured to simply "call" one or more processing/analysis functions to be applied to the data. By doing so, for example, a wide range of flexibility was allowed regarding signal processing techniques. As a result, one possible example can include an experienced user to "upload" his/her own signal processing script to the proposed application. However, in order to increase usability, the exemplary application can also be configured to come with "built-in" signal processing techniques, such as the exemplary custom-designed data analysis program (e.g., using MATLAB script) and the guided classifiers previously described.

An example of the Qt-based "all inclusive" program is described, which includes the following terms. In the context of the exemplary Qt-based "all inclusive" program, the term 'user' can refer to the operator of the application; 'subject' can refer to the individual whose data is being acquired; 'stimulus' can refer to any one instance of a stimulus presented to the subject; 'trial' can refer to the entire sequence of stimuli presented to the subject before processing the data; 'polymorphism' can refer to a condition when the same programming function performs differently when invoked in different contexts, e.g., possibly by different build classes; and 'virtual function; can refer to a function that is implemented differently in different subclasses of a superclass.

The "all inclusive" application system includes a client-server solution containing data acquisition, stimulus presentation, and data processing modules. For example, the client and the server lie on two different frameworks that can reside in the same or separate machines (e.g., local and/or remote). The client contains the data acquisition and stimulus presentation modules, while the server houses the data processing module. By structuring the client-server solution in this manner, the "all inclusive" application system can have the flexibility of being used on a multitude of devices. For example, a typical mobile device (e.g., a smartphone or tablet) normally does not have the computational power, speed, and battery life to process and analyze large amounts of data, e.g., such as that of EEG. In this exemplary case, the "all inclusive" application system can reside on two separate machines. For example, the stimulus presentation and data acquisition modules can reside in the mobile device itself, while the signal processing module can reside in a remote server. This remote signal processing module can receive and return data via internet (e.g., Wi-Fi and/or cellular data networks). By distributing the various modules, the "all inclusive" application system can be used on mobile devices in an efficient and usable manner. On the other hand, if an individual has access to a conventional computer (e.g., a laptop or desktop computer), they will be able to use the application locally, in which the modules (e.g., stimulus presentation, data acquisition, and signal processing) can reside within the same machine. This can be optimal in cases in which, for example, an individual does not have a reliable internet access connection.

Figure 17:
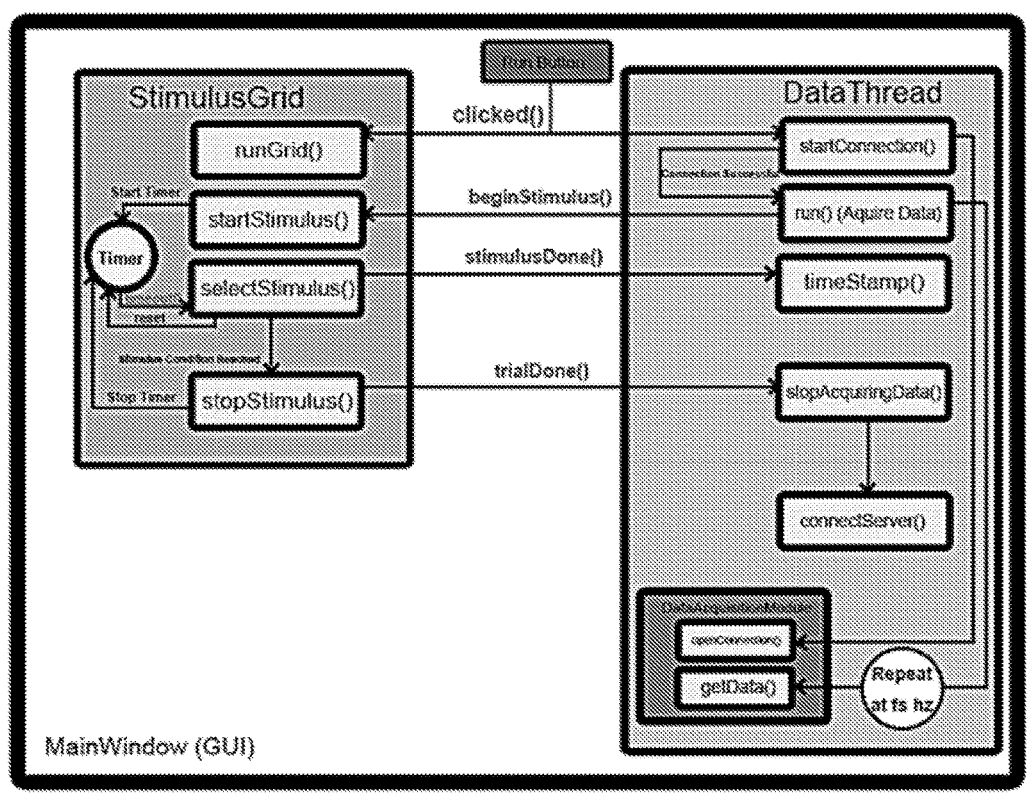
FIG. 17 shows a diagram illustrating the general architecture of an exemplary "all inclusive" application system that integrates modules of various classes, subclasses, and functions, to work in conjunction to create a user-friendly and automated system for stimulus presentation, data acquisition, and signal processing.

FIG. 17 shows a diagram illustrating an example of the general architecture of the exemplary "all inclusive" application system. The exemplary large boxes in the diagram (e.g., labeled "StimulusGrid", "DataThread", and "DataAcquisitionModule") are the core classes of the application. The smaller green boxes within the exemplary core class boxes correspond to the various functions of each class. The red edge labels represent Qt signals that are emitted from one class to another (e.g., such as 'clicked( )', 'beginStimulus( )', 'stimulusDone( )', 'trialDone( )', and 'timeout( )'). The black edge labels represent various events that may occur that cause a subsequent function to be invoked (e.g., such as 'Start Timer', 'reset', 'Stimulus Condition Reached', 'Stop Timer', and 'Connection Successful'). The "Run Button" box represents that actual "Run" button on the exemplary graphical user interface.

Within this exemplary framework, for example, two classes are defined representing the two core modules of client-side operation: StimulusGrid and DataThread. An additional class, DataAcquisitionModule, is instantiated within the DataThread module. These modules are instantiated in the MainWindow thread which creates connections for communication between the two threads and creates the graphical user interface.

The DataThread class is a subclass of Qt's QThread class, which is designed to run concurrently with the main thread of a Qt application. Thus this class will instantiate a DataAcquisitionModule for interfacing with different data acquisition hardware. To that end, the DataAcquisitionModule class can be subclassed to facilitate communication with different hardware devices. Two virtual functions (openConnection( ) and getData( ), existing within the DataAcquisitionModule class, designate functions that should be implemented within subclasses to reflect the hardware-specific interaction with the device. This provides generalization of all hardware device interfaces on the main thread of execution through the use of class polymorphism, which allows for a simple and effective extension of the application's hardware-dependent data acquisition capabilities.

The StimulusGrid class represents the stimulus paradigm that will be presented on the main thread to the subject. Instances of this class will run their stimulus presentation functions concurrently with the DataAcquisitionModule. This class can be subclassed to allow for rapid implementation and integration of stimulus paradigms, e.g., such as the auditory oddball, by allowing the main thread to exploit polymorphism for generalization of the stimulus structure. The exemplary architecture has modularized the functionality of the two core classes. The module interfaces defined above provide control over the interaction between classes and allow for extension/modification of implementation of each individual class function without affecting functionality of other classes. This allows for rapid and efficient extension of the StimulusGrid and DataAcquisitionModules.

Exemplary Code
Class: StimulusGrid
virtual void StimulusGrid::runGrid( ): Performs any initial configuration of the StimulusGrid that must be done before the stimulus cycle begins. Tasks performed in this function may include storing configuration values designated by the user on the GUI, initializing an array containing the order of stimuli to present to the subject or drawing the initial frame of the stimulus cycle to the graphical interface.

virtual void StimulusGrid::startStimulus( ): Begins the trial. For periodic stimuli that may repeat every x milliseconds, this function may initialize timing mechanisms such as an instance of Qt's QTimer. This function signals the selectStimulus( ) function to begin either by directly invoking it, or through a timing mechanism.

virtual void StimulusGrid::selectStimulus( ): Selects the next stimulus to present to the individual. This function selects stimuli either dynamically or by iterating through a predefined list of stimuli to be presented. Ideally, for example, this function should only perform the latter, as designating stimuli dynamically during runtime (e.g., invoking a random number generator for every iteration or dynamically searching a directory of images) may affect timing precision. This function will generally be invoked many times per trial as it is responsible for the presentation of stimuli. Every call to this function will also signal DataThread::timeStamp( ) to note the current packet number in the raw data stream in the timestamp QList, and note the marker of the selected stimulus in the marker QList.

virtual void StimulusGrid::stopStimulus( ): This function will be invoked when a trial is finished (e.g., when a predefined maximum limit of stimuli has been presented, or when a timing mechanism has expired). It will stop any initialized timers associated with the stimulus cycle, and will then signal DataThread::stopAcquiringData( ) to cease data acquisition.

Class: DataThread
int DataThread::startConnection( ): This function attempts to establish a connection with the specified device hardware via the interface with DataAcquisitionModule::openConnection( ) It will return 0 upon successful connection being established, and −1 otherwise.

void DataThread::run( ): In QThread, the run( ) function is designated as the concurrent function to be run when the QThread object is spawned for concurrent execution. In the context of this application, it repeatedly acquires data at a designated sampling rate via the interface at DataAcquisitionModule::getData( ). Also signals StimulusGrid::startStimulus( ) upon initial invocation to begin the stimulus cycle.

void DataThread::timeStamp( ): Notes the current position in the raw data stream in order to correlate acquired data samples with specific instances of presented stimuli. This function is invoked every time a new stimulus is presented to the subject via StimulusGrid::selectStimulus( ).

void DataThread::stopAcquiringData( ): This function is invoked by the stimulus thread when a trial is finished. This function frees any hardware connections and re-initializes counters to prepare for the next trial. It also invokes the connectServer( ) function.

void DataThread::connectServer( ): This function connects to the local or remote server module via a socket port. After a successful connection, the QList objects containing the marker, the timestamps, and the data are parsed into individual bytes and sent over to the server code. This function is invoked from DataThread::stopAcquiringData.

Class: DataAcquisitionModule
virtual void DataAcquisitionModule::openConnection( ): Attempts to open the connection to the specified acquisition hardware. This function will contain hardware-specific interface code to communicate with a given device.

virtual int DataAcquisitionModule::getData( ): Reads one data point from the incoming data stream of the specified data acquisition hardware. This function will contain hardware-specific interface code to communicate with and read from a given device.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system for evaluating neurological or neuropsychiatric disorders, comprising:
   a stimulus delivery device to produce a sequence of stimuli that is presented to a subject, wherein the stimuli includes at least one of a visual, auditory, olfactory, tactile, or gustatory stimulating medium;
   a sensor device interfaced to the subject to detect physiological signals exhibited by the subject before, during, and after a presentation of the sequence of stimuli, the sequence of stimuli based on a cognitive-sensory profile category indicative of one or more aspects of cognitive or sensory functions associated with a neurological or neuropsychiatric disorder;
   a data processing system in communication with the sensor device and structured to include one or more memory units and one or more processors configured to process the physiological signals as physiological data to generate an information set including one or more quantitative values associated with the cognitive-sensory profile category, the one or more quantitative values including a quantitative score depicting a level of the subject's vulnerability to or progressive pathology of the neurological or neuropsychiatric disorder; and
   a brain-machine interface module in communication with the data processing system and the stimulus delivery device to adaptively modify the sequence of stimuli individualized with respect to the subject during an on-going presentation of the stimuli to the subject based on data associated with or derived from the generated information set.

2. The system as in claim 1, wherein the data processing system includes:
   a local computer located proximate and in communication with the sensor device to receive the detected physiological signals from the sensor device, the local computer configured to conduct initial processing of the detected physiological signals to produce initial physiological signal data, and a remote computer in communication with the local computer via a communication network or link to receive the initial physiological signal data from the local computer and to process the initial physiological signal data to generate the information set including one or more quantitative values associated with the cognitive-sensory profile category.

3. The system as in claim 2, wherein the brain machine interface module is resident on the local computer in communication with the stimulus delivery device and is configured to determine the sequence of stimuli to be presented to the subject based on the cognitive-sensory profile category.

4. The system as in claim 3, wherein the brain machine interface module resident on the local computer is configured to receive data associated with or derived from the generated information set and to modify administration of a treatment associated with the neurological or neuropsychiatric disorder to the subject during the on-going presentation of the sequence of stimuli that is individualized with respect to the subject.

5. The system as in claim 1, wherein the stimulus delivery device includes one or both of a display screen to generate a sequence of images and a speaker to generate a sequence of sounds.

6. The system as in claim 1, wherein the stimulus delivery device includes an actuator to generate a sequence of at least one of olfactory, tactile, or gustatory stimuli.

7. The system as in claim 1, wherein the neurological or neuropsychiatric disorder includes at least one of attention deficit hyperactivity disorder (ADHD), autism spectrum disorder (ASD), Alzheimer's disease, dementia, depression, bipolar disorder, schizophrenia, epilepsy, multiple sclerosis (MS), Parkinson's disease, or Huntington's disease.

8. The system as in claim 1, wherein the quantitative score depicts the level at a particular time corresponding to the acquiring of the physiological signals of the subject.

9. The system as in claim 1, wherein the one or more aspects of cognitive or sensory functions include at least one of attention, memory, learning ability, confabulation characteristics, pattern integration ability, semantic integration ability, target detection ability, emotional valence, preference, or awareness state.

10. The system as in claim 1, wherein the subject is undergoing a treatment to the neurological or neuropsychiatric disorder during the detection of the subject's physiological signals.

11. The system as in claim 10, wherein the data processing system is configured to process the physiological data to generate the information set to include one or more quantitative values associated with the cognitive-sensory profile category indicative of the efficacy of the treatment for the subject.

12. The system as in claim 11, wherein the treatment includes at least one of a pharmacological agent, electroconvulsive therapy, a cognitive rehabilitation therapy, or a surgical treatment, and wherein the data processing system is configured to produce a machine procedure based on the generated information set, and wherein the machine procedure actuates another device or system to administer the treatment derived from information contained within the generated information set.

13. The system as in claim 1, wherein the sensor device includes a flexible substrate, sensor electrodes on the flexible substrate, and a transmitter unit in electrical communication with the electrodes and on the flexible substrate, wherein the sensor device is configured as one or more wearable patches worn on the subject's scalp to record electroencephalogram (EEG) signals and transmit the recorded EEG signals to at least one of the data processing unit or a remote computer system.

14. The system as in claim 1, wherein the sensor device includes electrodes attachable to the subject to receive electrical signals from the subject.

15. The system as in claim 1, wherein the sensor device includes an imaging device that captures images of the subject indicating a motion or movement of the subject.

16. The system as in claim 15, wherein the imaging device captures eye movement of the subject.

* * * * *